US011134953B2

(12) United States Patent
Solaun

(10) Patent No.: US 11,134,953 B2
(45) Date of Patent: Oct. 5, 2021

(54) ADHESIVE COVER OCCLUDING DEVICE FOR ANEURYSM TREATMENT

(71) Applicant: DePuy Synthes Products, Inc., Raynham, MA (US)

(72) Inventor: Daniel Solaun, Raynham, MA (US)

(73) Assignee: DEPUY SYNTHES PRODUCTS, INC., Raynham, MA (US)

(*) Notice: Subject to any disclaimer, the term of this patent is extended or adjusted under 35 U.S.C. 154(b) by 88 days.

(21) Appl. No.: 16/269,209

(22) Filed: Feb. 6, 2019

(65) Prior Publication Data
US 2020/0246016 A1   Aug. 6, 2020

(51) Int. Cl.
*A61B 17/12* (2006.01)
*A61F 2/82* (2013.01)

(52) U.S. Cl.
CPC .. *A61B 17/12113* (2013.01); *A61B 17/12168* (2013.01); *A61B 17/12186* (2013.01);
(Continued)

(58) Field of Classification Search
CPC ........ A61B 17/12109; A61B 17/12113; A61B 17/12168; A61B 17/12181; A61B 17/12186; A61B 17/1219; A61B 17/12195; A61B 2017/1205; A61B 17/0057; A61B 17/12022; A61B 17/12027; A61B 17/12031; A61B 17/12036; A61B 2017/00575; A61B 2017/00597;
(Continued)

(56) References Cited

U.S. PATENT DOCUMENTS

| 2,849,002 A | 8/1958 | Oddo |
| 3,480,017 A | 11/1969 | Shute |

(Continued)

FOREIGN PATENT DOCUMENTS

| CA | 2395796 A1 | 7/2001 |
| CA | 2 431 594 A1 | 9/2002 |

(Continued)

OTHER PUBLICATIONS

Extended European Search Report issued in corresponding European Patent Application No. 19 21 5277 dated May 12, 2020.
(Continued)

*Primary Examiner* — Diane D Yabut
*Assistant Examiner* — Christian D Knauss
(74) *Attorney, Agent, or Firm* — Troutman Pepper Hamilton Sanders LLP

(57) ABSTRACT

The device includes a net portion for occluding an aneurysm neck and an adhesive to secure the net portion. The device can further include a channel orifice opening in the net portion, and an agent channel for delivering a rapid-curing agent through the orifice into the aneurysm. Devices can be delivered through a catheter to the aneurysm, the net can expand to occlude the aneurysm neck, the net can be adhered to the aneurysm neck. In devices including a channel orifice and agent channel, the rapid-curing agent can be injected into the aneurysm. During injection of the rapid-curing agent, the net portion can create a barrier to inhibit the rapid-curing agent from exiting the aneurysm. After injection of the coagulation agent, portions of the treatment device, excluding the net portion, can be extracted from the patient.

18 Claims, 10 Drawing Sheets

(52) U.S. Cl.
CPC ....... *A61B 17/1214* (2013.01); *A61B 17/1219* (2013.01); *A61B 2017/1205* (2013.01); *A61F 2002/823* (2013.01); *A61F 2250/0067* (2013.01)

(58) Field of Classification Search
CPC .. A61B 2017/0061; A61B 2017/00623; A61B 2017/0065; A61B 2017/00654; A61B 2017/00659; A61F 2002/823; A61F 2250/0067
See application file for complete search history.

(56) References Cited

U.S. PATENT DOCUMENTS

| | | |
|---|---|---|
| 4,085,757 A | 4/1978 | Pevsner |
| 4,282,875 A | 4/1981 | Serbinenko et al. |
| 4,364,392 A | 12/1982 | Strother et al. |
| 4,395,806 A | 8/1983 | Wonder et al. |
| 4,517,979 A | 5/1985 | Pecenka |
| 4,545,367 A | 10/1985 | Tucci |
| 4,836,204 A | 6/1989 | Landymore et al. |
| 4,991,602 A | 2/1991 | Amplatz et al. |
| 5,002,556 A | 3/1991 | Ishida et al. |
| 5,025,060 A | 6/1991 | Yabuta et al. |
| 5,065,772 A | 11/1991 | Cox, Jr. |
| 5,067,489 A | 11/1991 | Lind |
| 5,122,136 A | 6/1992 | Guglielmi et al. |
| 5,192,301 A | 3/1993 | Kamiya et al. |
| 5,261,916 A | 11/1993 | Engelson |
| 5,304,195 A | 4/1994 | Twyford, Jr. et al. |
| 5,334,210 A | 8/1994 | Gianturco |
| 5,350,397 A | 9/1994 | Palermo |
| 5,423,829 A | 6/1995 | Pham et al. |
| 5,624,449 A | 4/1997 | Pham et al. |
| 5,645,558 A | 7/1997 | Horton |
| 5,733,294 A | 3/1998 | Forber et al. |
| 5,891,128 A | 4/1999 | Chin et al. |
| 5,916,235 A | 6/1999 | Guglielmi |
| 5,928,260 A | 7/1999 | Chin et al. |
| 5,935,148 A | 8/1999 | Villar |
| 5,941,249 A | 8/1999 | Maynard |
| 5,951,599 A | 9/1999 | McCrory |
| 5,964,797 A | 10/1999 | Ho |
| 6,007,573 A | 12/1999 | Wallace et al. |
| 6,024,756 A | 2/2000 | Pham |
| 6,036,720 A | 3/2000 | Abrams |
| 6,063,070 A | 5/2000 | Eder |
| 6,063,100 A | 5/2000 | Diaz et al. |
| 6,063,104 A | 5/2000 | Villar |
| 6,080,191 A | 6/2000 | Thaler |
| 6,086,577 A | 7/2000 | Ken et al. |
| 6,096,021 A | 8/2000 | Helm et al. |
| 6,113,609 A | 9/2000 | Adams |
| 6,123,714 A | 9/2000 | Gia et al. |
| 6,168,615 B1 | 1/2001 | Ken |
| 6,168,622 B1 | 1/2001 | Mazzocchi |
| 6,193,708 B1 | 2/2001 | Ken et al. |
| 6,221,086 B1 | 4/2001 | Forber |
| 6,270,515 B1 | 8/2001 | Linden et al. |
| 6,315,787 B1 | 11/2001 | Tsugita et al. |
| 6,331,184 B1 | 12/2001 | Abrams |
| 6,334,048 B1 | 12/2001 | Edvardsson et al. |
| 6,346,117 B1 | 2/2002 | Greenhalgh |
| 6,350,270 B1 | 2/2002 | Roue |
| 6,375,606 B1 | 4/2002 | Garbaldi et al. |
| 6,375,668 B1 | 4/2002 | Gifford |
| 6,379,329 B1 | 4/2002 | Naglreiter et al. |
| 6,391,037 B1 | 5/2002 | Greenhalgh |
| 6,419,686 B1 | 7/2002 | McLeod et al. |
| 6,428,558 B1 | 8/2002 | Jones |
| 6,454,780 B1 | 9/2002 | Wallace |
| 6,463,317 B1 | 10/2002 | Kucharczyk et al. |
| 6,506,204 B2 | 1/2003 | Mazzocchi |
| 6,527,919 B1 | 3/2003 | Roth |
| 6,547,804 B2 | 4/2003 | Porter et al. |
| 6,551,303 B1 * | 4/2003 | Van Tassel ......... A61B 17/0057 128/898 |
| 6,569,179 B2 | 5/2003 | Teoh |
| 6,569,190 B2 | 5/2003 | Whalen, II et al. |
| 6,572,628 B2 | 6/2003 | Dominguez |
| 6,589,230 B2 | 7/2003 | Gia et al. |
| 6,589,256 B2 | 7/2003 | Forber |
| 6,605,102 B1 | 8/2003 | Mazzocchi et al. |
| 6,620,152 B2 | 9/2003 | Guglielmi |
| 6,669,719 B2 | 12/2003 | Wallace et al. |
| 6,689,159 B2 | 2/2004 | Lau et al. |
| 6,746,468 B1 | 6/2004 | Sepetka |
| 6,780,196 B2 | 8/2004 | Chin et al. |
| 6,802,851 B2 | 10/2004 | Jones |
| 6,811,560 B2 | 11/2004 | Jones |
| 6,833,003 B2 | 12/2004 | Jones et al. |
| 6,846,316 B2 | 1/2005 | Abrams |
| 6,849,081 B2 | 2/2005 | Sepetka et al. |
| 6,855,154 B2 | 2/2005 | Abdel-Gawwad |
| 6,949,116 B2 | 9/2005 | Solymar et al. |
| 6,964,657 B2 | 11/2005 | Cragg et al. |
| 6,964,671 B2 | 11/2005 | Cheng |
| 6,994,711 B2 | 2/2006 | Hieshima et al. |
| 7,044,134 B2 | 5/2006 | Khairkhahan et al. |
| 7,083,632 B2 | 8/2006 | Avellanet |
| 7,093,527 B2 | 8/2006 | Rapaport et al. |
| 7,128,736 B1 | 10/2006 | Abrams et al. |
| 7,152,605 B2 | 12/2006 | Khairkhahan et al. |
| 7,153,323 B1 | 12/2006 | Teoh |
| 7,195,636 B2 | 3/2007 | Avellanet et al. |
| 7,229,454 B2 | 6/2007 | Tran et al. |
| 7,229,461 B2 | 6/2007 | Chin et al. |
| 7,309,345 B2 | 12/2007 | Wallace |
| 7,371,249 B2 | 5/2008 | Douk et al. |
| 7,410,482 B2 | 8/2008 | Murphy et al. |
| 7,572,288 B2 | 8/2009 | Cox |
| 7,597,704 B2 | 10/2009 | Frazier et al. |
| 7,608,088 B2 | 10/2009 | Jones |
| 7,695,488 B2 | 4/2010 | Berenstein et al. |
| 7,713,264 B2 | 5/2010 | Murphy |
| 7,744,652 B2 | 6/2010 | Morsi |
| 7,892,248 B2 | 2/2011 | Tran |
| 7,985,238 B2 | 7/2011 | Balgobin et al. |
| RE42,758 E | 9/2011 | Ken |
| 8,016,852 B2 | 9/2011 | Ho |
| 8,021,416 B2 | 9/2011 | Abrams |
| 8,025,668 B2 | 9/2011 | McCartney |
| 8,034,061 B2 | 10/2011 | Amplatz et al. |
| 8,048,145 B2 | 11/2011 | Evans et al. |
| 8,062,325 B2 | 11/2011 | Mitelberg et al. |
| 8,075,585 B2 | 12/2011 | Lee et al. |
| 8,142,456 B2 | 3/2012 | Rosqueta et al. |
| 8,221,483 B2 | 7/2012 | Ford et al. |
| 8,261,648 B1 | 9/2012 | Marchand et al. |
| 8,267,923 B2 | 9/2012 | Murphy |
| 8,361,106 B2 | 1/2013 | Solar et al. |
| 8,361,138 B2 | 1/2013 | Adams |
| 8,372,114 B2 | 2/2013 | Hines |
| 8,398,671 B2 | 3/2013 | Chen |
| 8,430,012 B1 | 4/2013 | Marchand |
| 8,454,633 B2 | 6/2013 | Amplatz et al. |
| 8,523,897 B2 | 9/2013 | van der Burg et al. |
| 8,523,902 B2 | 9/2013 | Heaven et al. |
| 8,551,132 B2 | 10/2013 | Eskridge et al. |
| 8,777,974 B2 | 7/2014 | Amplatz et al. |
| 8,900,304 B1 | 12/2014 | Alobaid |
| 8,992,568 B2 | 3/2015 | Duggal et al. |
| 8,998,947 B2 | 3/2015 | Aboytes et al. |
| 8,974,512 B2 | 4/2015 | Aboytes et al. |
| 9,055,948 B2 | 6/2015 | Jaeger et al. |
| 9,107,670 B2 | 8/2015 | Hannes |
| 9,161,758 B2 | 10/2015 | Figulla et al. |
| 9,232,992 B2 | 1/2016 | Heidner et al. |
| 9,259,337 B2 | 2/2016 | Cox et al. |
| 9,314,326 B2 | 4/2016 | Wallace et al. |
| 9,351,715 B2 | 5/2016 | Mach |
| 9,414,842 B2 | 8/2016 | Glimsdale et al. |
| 9,526,813 B2 | 12/2016 | Cohn et al. |

(56) References Cited

U.S. PATENT DOCUMENTS

| | | |
|---|---|---|
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,096 B2 | 2/2017 | Fogarty |
| 9,561,125 B2 | 2/2017 | Bowman et al. |
| 9,572,982 B2 | 2/2017 | Burnes et al. |
| 9,579,104 B2 | 2/2017 | Beckham et al. |
| 9,579,484 B2 | 2/2017 | Barnell |
| 9,585,642 B2 | 3/2017 | Dinsmoor et al. |
| 9,585,669 B2 | 3/2017 | Becking et al. |
| 9,615,832 B2 | 4/2017 | Bose et al. |
| 9,615,951 B2 | 4/2017 | Bennett et al. |
| 9,622,753 B2 | 4/2017 | Cox |
| 9,629,635 B2 | 4/2017 | Hewitt et al. |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign |
| 9,681,861 B2 | 6/2017 | Heisel et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Paterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 9,918,720 B2 | 3/2018 | Marchand et al. |
| 9,955,976 B2 | 5/2018 | Hewitt et al. |
| 10,130,372 B2 | 11/2018 | Griffin |
| 10,307,148 B2 | 6/2019 | Heisel et al. |
| 10,327,781 B2 | 6/2019 | Divino et al. |
| 10,342,546 B2 | 7/2019 | Sepetka et al. |
| 10,517,604 B2 | 12/2019 | Bowman et al. |
| 10,716,573 B2 | 7/2020 | Connor |
| 2002/0068974 A1 | 6/2002 | Kuslich et al. |
| 2002/0082638 A1 | 6/2002 | Porter et al. |
| 2002/0143349 A1 | 10/2002 | Gifford, III et al. |
| 2002/0147497 A1 | 10/2002 | Belef et al. |
| 2002/0188314 A1 | 12/2002 | Anderson et al. |
| 2003/0028209 A1 | 2/2003 | Teoh et al. |
| 2003/0120337 A1 | 6/2003 | Van Tassel et al. |
| 2003/0171739 A1 | 9/2003 | Murphy |
| 2003/0176884 A1 | 9/2003 | Berrada et al. |
| 2003/0181927 A1 | 9/2003 | Wallace |
| 2003/0181945 A1 | 9/2003 | Opolski |
| 2003/0195553 A1 | 10/2003 | Wallace |
| 2003/0216772 A1 | 11/2003 | Konya |
| 2004/0034366 A1 | 2/2004 | van der Burg et al. |
| 2004/0034386 A1 | 2/2004 | Fulton et al. |
| 2004/0044391 A1 | 3/2004 | Porter |
| 2004/0087998 A1 | 5/2004 | Lee et al. |
| 2004/0098027 A1 | 5/2004 | Teoh et al. |
| 2004/0127935 A1 | 7/2004 | Van Tassel et al. |
| 2004/0133222 A1 | 7/2004 | Tran et al. |
| 2004/0153120 A1 | 8/2004 | Seifert et al. |
| 2004/0210297 A1 | 10/2004 | Lin et al. |
| 2004/0254594 A1 | 12/2004 | Alfaro |
| 2005/0021016 A1 | 1/2005 | Malecki et al. |
| 2005/0021072 A1 | 1/2005 | Wallace |
| 2005/0159771 A1 | 7/2005 | Petersen |
| 2005/0177103 A1 | 8/2005 | Hunter et al. |
| 2005/0251200 A1 | 11/2005 | Porter |
| 2006/0052816 A1 | 3/2006 | Bates et al. |
| 2006/0058735 A1 | 3/2006 | Lesh |
| 2006/0064151 A1 | 3/2006 | Gutterman et al. |
| 2006/0106421 A1 | 5/2006 | Teoh |
| 2006/0155323 A1 | 7/2006 | Porter et al. |
| 2006/0155367 A1 | 7/2006 | Hines |
| 2006/0167494 A1 | 7/2006 | Suddaby |
| 2006/0247572 A1 | 11/2006 | McCartney |
| 2007/0088387 A1 | 4/2007 | Eskridge et al. |
| 2007/0106311 A1 | 5/2007 | Wallace et al. |
| 2007/0208376 A1 | 6/2007 | Meng |
| 2007/0162071 A1 | 7/2007 | Burkett et al. |
| 2007/0167876 A1 | 7/2007 | Euteneuer et al. |
| 2007/0173928 A1 | 7/2007 | Morsi |
| 2007/0186933 A1 | 8/2007 | Domingo |
| 2007/0191884 A1 | 8/2007 | Eskridge et al. |
| 2007/0233188 A1* | 10/2007 | Hunt .................. A61B 17/0487 606/228 |
| 2007/0265656 A1 | 11/2007 | Amplatz et al. |
| 2007/0288083 A1 | 12/2007 | Hines |
| 2008/0097495 A1 | 4/2008 | Feller, III et al. |
| 2008/0103505 A1 | 5/2008 | Fransen |
| 2008/0281350 A1 | 11/2008 | Sepetka et al. |
| 2009/0036877 A1 | 2/2009 | Nardone et al. |
| 2009/0062841 A1 | 3/2009 | Amplatz et al. |
| 2009/0099647 A1 | 4/2009 | Glimsdale |
| 2009/0227983 A1 | 9/2009 | Griffin et al. |
| 2009/0281557 A1 | 11/2009 | Sander et al. |
| 2009/0287291 A1 | 11/2009 | Becking et al. |
| 2009/0287297 A1 | 11/2009 | Cox |
| 2009/0318941 A1 | 12/2009 | Sepetka |
| 2010/0023046 A1 | 1/2010 | Heidner et al. |
| 2010/0023048 A1 | 1/2010 | Mach |
| 2010/0063573 A1 | 3/2010 | Hijlkema |
| 2010/0063582 A1 | 3/2010 | Rudakov |
| 2010/0069948 A1 | 3/2010 | Veznedaroglu et al. |
| 2010/0168781 A1 | 7/2010 | Berenstein |
| 2010/0211156 A1 | 8/2010 | Linder et al. |
| 2010/0324649 A1 | 12/2010 | Mattsson et al. |
| 2011/0046658 A1 | 2/2011 | Conner et al. |
| 2011/0054519 A1 | 3/2011 | Neuss |
| 2011/0112588 A1 | 5/2011 | Linderman et al. |
| 2011/0137317 A1 | 6/2011 | O'Halloran et al. |
| 2011/0152993 A1 | 6/2011 | Marchand et al. |
| 2011/0196413 A1 | 8/2011 | Wallace |
| 2011/0319978 A1 | 12/2011 | Schaffer |
| 2012/0010644 A1 | 1/2012 | Sideris et al. |
| 2012/0071911 A1 | 3/2012 | Sadasivan |
| 2012/0165732 A1 | 6/2012 | Müller |
| 2012/0191123 A1 | 7/2012 | Brister et al. |
| 2012/0283768 A1 | 11/2012 | Cox et al. |
| 2012/0310270 A1 | 12/2012 | Murphy |
| 2012/0323267 A1 | 12/2012 | Ren |
| 2012/0330341 A1 | 12/2012 | Becking et al. |
| 2013/0035665 A1 | 2/2013 | Chu |
| 2013/0035712 A1 | 2/2013 | Theobald et al. |
| 2013/0066357 A1 | 3/2013 | Aboytes et al. |
| 2013/0079864 A1 | 3/2013 | Boden |
| 2013/0110066 A1 | 5/2013 | Sharma et al. |
| 2013/0204351 A1 | 8/2013 | Cox et al. |

(56) References Cited

U.S. PATENT DOCUMENTS

| | | |
|---|---|---|
| 2013/0211495 A1 | 8/2013 | Halden et al. |
| 2013/0261658 A1 | 10/2013 | Lorenzo et al. |
| 2013/0261730 A1 | 10/2013 | Bose et al. |
| 2013/0274863 A1 | 10/2013 | Cox et al. |
| 2013/0345738 A1 | 12/2013 | Eskridge |
| 2014/0005714 A1 | 1/2014 | Quick et al. |
| 2014/0012307 A1 | 1/2014 | Franano et al. |
| 2014/0012363 A1 | 1/2014 | Franano et al. |
| 2014/0018838 A1 | 1/2014 | Franano et al. |
| 2014/0135812 A1 | 5/2014 | Divino et al. |
| 2014/0200607 A1 | 7/2014 | Sepetka et al. |
| 2014/0257360 A1 | 9/2014 | Keillor |
| 2014/0277013 A1 | 9/2014 | Sepetka et al. |
| 2014/0358178 A1 | 12/2014 | Hewitt et al. |
| 2015/0057703 A1 | 2/2015 | Ryan et al. |
| 2015/0209050 A1 | 7/2015 | Aboytes et al. |
| 2015/0272589 A1 | 10/2015 | Lorenzo |
| 2015/0313605 A1 | 11/2015 | Griffin |
| 2015/0342613 A1 | 12/2015 | Aboytes et al. |
| 2015/0374483 A1 | 12/2015 | Janardhan et al. |
| 2016/0022445 A1 | 1/2016 | Ruvalcaba et al. |
| 2016/0030050 A1 | 2/2016 | Franano et al. |
| 2016/0192912 A1* | 7/2016 | Kassab ............ A61B 17/00491 606/200 |
| 2016/0249934 A1 | 9/2016 | Hewitt et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079661 A1 | 3/2017 | Bardsley et al. |
| 2017/0079662 A1 | 3/2017 | Rhee et al. |
| 2017/0079671 A1 | 3/2017 | Morero et al. |
| 2017/0079680 A1 | 3/2017 | Bowman |
| 2017/0079717 A1 | 3/2017 | Walsh et al. |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo et al. |
| 2017/0113023 A1 | 4/2017 | Steingisser et al. |
| 2017/0114350 A1 | 4/2017 | dos Santos et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340333 A1 | 11/2017 | Badruddin et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2018/0140305 A1 | 5/2018 | Connor |
| 2018/0242979 A1 | 8/2018 | Lorenzo |
| 2018/0303531 A1 | 10/2018 | Sanders et al. |
| 2018/0338767 A1* | 11/2018 | Dasnurkar ....... A61B 17/12168 |
| 2019/0008522 A1 | 1/2019 | Lorenzo |
| 2019/0223878 A1 | 1/2019 | Lorenzo et al. |
| 2019/0110796 A1 | 4/2019 | Jayaraman |
| 2019/0192162 A1 | 6/2019 | Lorenzo |
| 2019/0192167 A1 | 6/2019 | Lorenzo |
| 2019/0192168 A1 | 6/2019 | Lorenzo |
| 2019/0223879 A1 | 7/2019 | Jayaraman |
| 2019/0223881 A1 | 9/2019 | Hewitt et al. |
| 2019/0328398 A1 | 10/2019 | Lorenzo |
| 2019/0365385 A1 | 12/2019 | Gorochow et al. |
| 2020/0268365 A1 | 8/2020 | Hebert et al. |

FOREIGN PATENT DOCUMENTS

| | | |
|---|---|---|
| CA | 2598048 A1 | 5/2008 |
| CN | 204 683 687 U | 7/2015 |
| DE | 102008015781 A1 | 10/2009 |
| DE | 102010053111 A1 | 6/2012 |
| DE | 102009058132 B4 | 7/2014 |
| DE | 10 2013 106031 A1 | 12/2014 |
| DE | 202008018523 U1 | 4/2015 |
| DE | 102011102955 B4 | 5/2018 |
| EP | 902704 B1 | 3/1999 |
| EP | 1054635 B1 | 11/2000 |
| EP | 1295563 A1 | 3/2003 |
| EP | 1441649 B1 | 8/2004 |
| EP | 1483009 B1 | 12/2004 |
| EP | 1527753 B1 | 5/2005 |
| EP | 1569565 B1 | 9/2005 |
| EP | 1574169 B1 | 9/2005 |
| EP | 1494619 B1 | 1/2006 |
| EP | 1633275 B1 | 3/2006 |
| EP | 1659988 B1 | 5/2006 |
| EP | 1725185 B1 | 11/2006 |
| EP | 1862122 A1 | 12/2007 |
| EP | 1923005 B1 | 5/2008 |
| EP | 2063791 B1 | 6/2009 |
| EP | 2134263 B1 | 12/2009 |
| EP | 2157937 B1 | 3/2010 |
| EP | 2266456 A1 | 12/2010 |
| EP | 2324775 B1 | 5/2011 |
| EP | 2367482 B1 | 9/2011 |
| EP | 2387951 B1 | 11/2011 |
| EP | 2460476 A2 | 6/2012 |
| EP | 2468349 A1 | 6/2012 |

(56) References Cited

FOREIGN PATENT DOCUMENTS

| | | | |
|---|---|---|---|
| EP | 2543345 A1 | 1/2013 |
| EP | 2567663 A1 | 3/2013 |
| EP | 2617386 A1 | 7/2013 |
| EP | 2623039 A1 | 8/2013 |
| EP | 2647343 A2 | 10/2013 |
| EP | 2848211 A1 | 3/2015 |
| EP | 2854704 B1 | 4/2015 |
| EP | 2923674 B1 | 9/2015 |
| EP | 2926744 A1 | 10/2015 |
| EP | 3146916 A1 | 3/2017 |
| EP | 3501429 A1 | 6/2019 |
| EP | 3517055 A1 | 7/2019 |
| JP | H04-47415 U | 4/1992 |
| JP | H07-37200 U | 7/1995 |
| JP | 2006-509578 A | 3/2006 |
| JP | 2013-509972 A | 3/2013 |
| JP | 2013537069 A | 9/2013 |
| JP | 2016-502925 A | 2/2015 |
| WO | WO 9641589 A1 | 12/1996 |
| WO | WO 9905977 A1 | 2/1999 |
| WO | WO 9908607 A1 | 2/1999 |
| WO | WO 9930640 A1 | 6/1999 |
| WO | WO 2003073961 A1 | 9/2003 |
| WO | WO 03/086240 A1 | 10/2003 |
| WO | 2005020822 A1 | 3/2005 |
| WO | 2005/074814 A2 | 8/2005 |
| WO | WO 2005117718 A1 | 12/2005 |
| WO | WO 2006034149 A2 | 3/2006 |
| WO | WO 2006052322 A2 | 5/2006 |
| WO | 2007/076480 A2 | 7/2007 |
| WO | WO 2008150346 A1 | 12/2008 |
| WO | WO 2008151204 A1 | 12/2008 |
| WO | WO 2009048700 A1 | 4/2009 |
| WO | WO 2009105365 A1 | 8/2009 |
| WO | WO 2009132045 A2 | 10/2009 |
| WO | WO 2009135166 A2 | 11/2009 |
| WO | WO 2010030991 A1 | 3/2010 |
| WO | WO 2011057002 A2 | 5/2011 |
| WO | WO 2012032030 A1 | 3/2012 |
| WO | 2012099704 A2 | 7/2012 |
| WO | WO 2012099909 A2 | 7/2012 |
| WO | WO 2012113554 A1 | 8/2012 |
| WO | WO 2013016618 A2 | 1/2013 |
| WO | WO 2013025711 A1 | 2/2013 |
| WO | WO 2013109309 A1 | 7/2013 |
| WO | WO 2013159065 | 10/2013 |
| WO | WO 2013162817 A1 | 10/2013 |
| WO | WO 2014029835 A1 | 2/2014 |
| WO | WO 2014078286 A1 | 5/2014 |
| WO | WO 2014110589 A1 | 7/2014 |
| WO | WO 2014137467 A1 | 9/2014 |
| WO | WO 2015073704 A1 | 5/2015 |
| WO | WO 2015160721 A1 | 10/2015 |
| WO | WO 2015166013 A1 | 11/2015 |
| WO | WO 2015171268 A2 | 11/2015 |
| WO | WO 2015184075 A1 | 12/2015 |
| WO | WO 2015187196 A1 | 12/2015 |
| WO | WO 2016044647 A2 | 3/2016 |
| WO | WO 2016107357 A1 | 7/2016 |
| WO | WO 2016137997 A1 | 9/2016 |
| WO | WO 2017/161283 A1 | 9/2017 |
| WO | WO 2018051187 A1 | 3/2018 |
| WO | WO 2012/034135 A1 | 3/2021 |

OTHER PUBLICATIONS

Extended European Search Report issued in corresponding European Patent Application No. 20 15 5664 dated Mar. 30, 2020.

Altes et al., Creation of Saccular Aneurysms in the Rabbit: A Model Suitable for Testing Endovascular Devices. AJR 2000; 174: 349-354.

Schaffer, Advanced Materials & Processes, Oct. 2002, pp. 51-54.

* cited by examiner

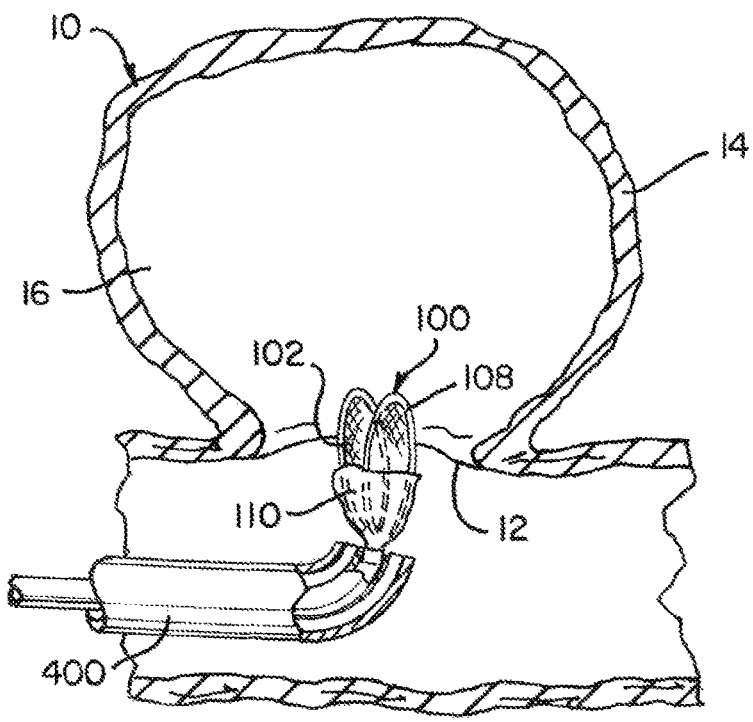
FIG. 2A
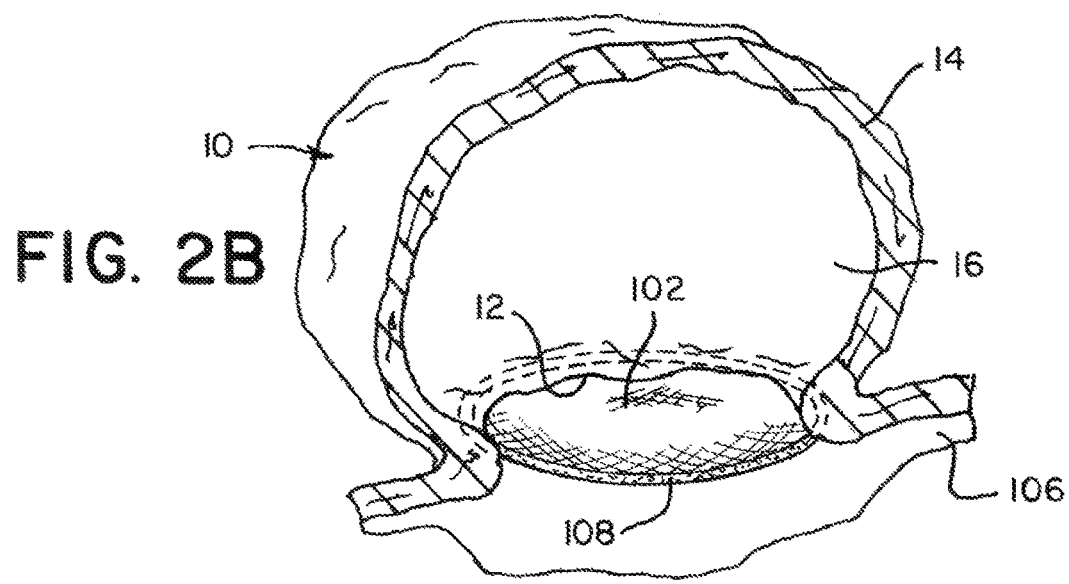
FIG. 2B
FIG. 3A
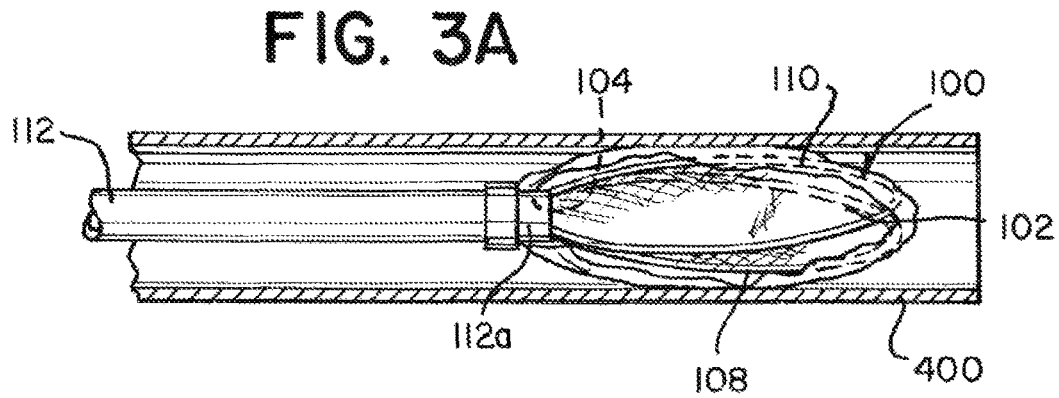

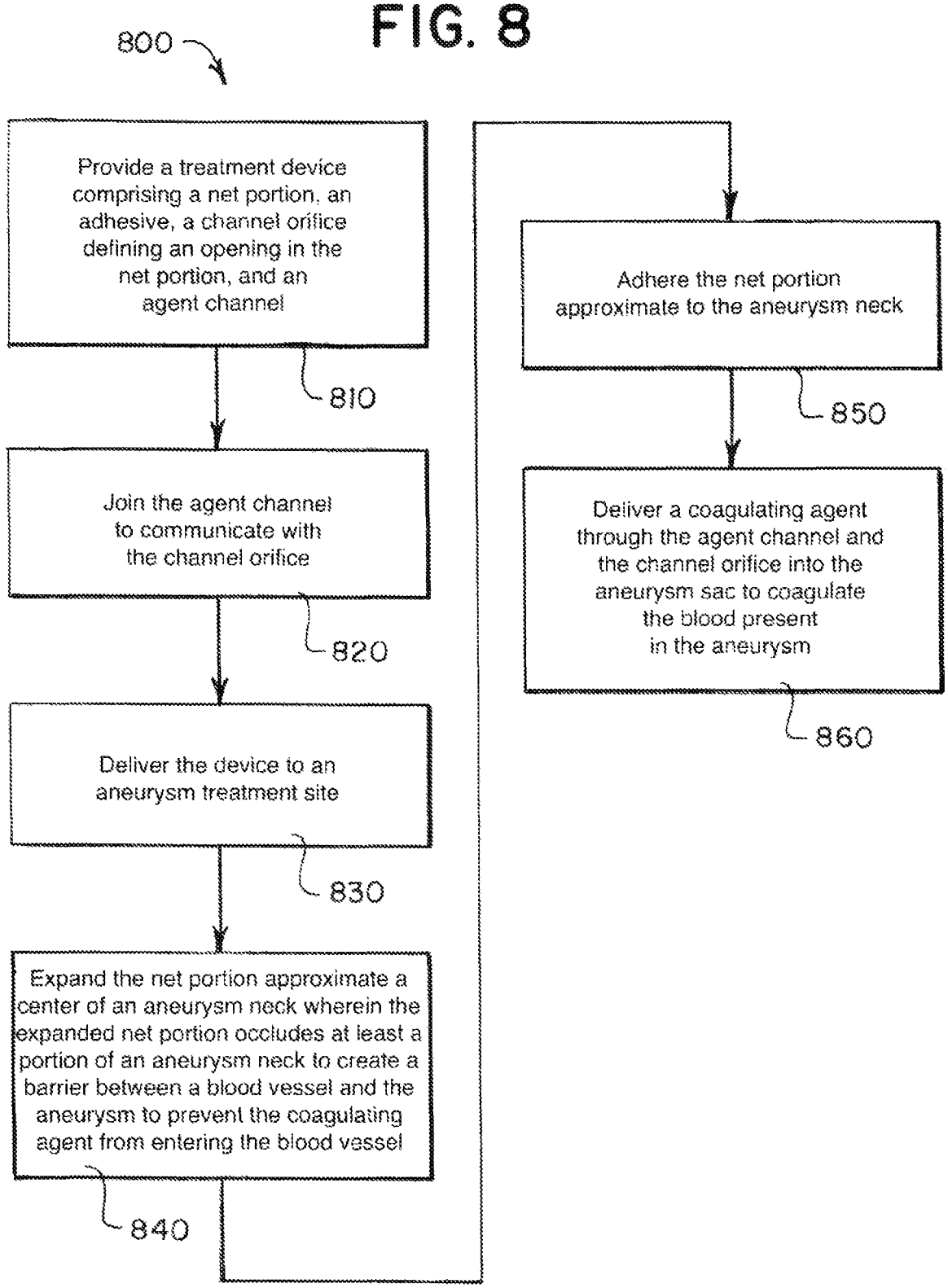

ADHESIVE COVER OCCLUDING DEVICE FOR ANEURYSM TREATMENT

FIELD OF INVENTION

The present invention generally relates to medical instruments, and more particularly, to treatment devices for aneurysm therapy.

BACKGROUND

Aneurysms can be complicated and difficult to treat. For example, treatment access can be limited or unavailable when an aneurysm is located proximate critical tissues. Such factors are of particular concern with cranial aneurysms due to the brain tissue surrounding cranial vessels and the corresponding limited treatment access.

Prior solutions have included endovascular treatment access whereby an internal volume of the aneurysm sac is removed or excluded from arterial blood pressure and flow. In this respect, because the interior walls of the aneurysm can continue being subjected to flow of blood and related pressure, aneurysm rupture remains possible.

Alternative to endovascular or other surgical approaches can include occlusive devices. Such devices have typically incorporated multiple embolic coils that are delivered to the vasculature using microcatheter delivery systems. For example, when treating cranial aneurysms, a delivery catheter with embolic coils is typically first inserted into non-cranial vasculature through a femoral artery in the hip or groin area. Thereafter, the catheter is guided to a location of interest within the cranium. The sac of the aneurysm can then be filled with the embolic material to create a thrombotic mass that protects the arterial walls from blood flow and related pressure. However, such occlusive devices do have certain shortcomings, including mass effect, which can cause compression on the brain and its nerves. Obtaining an embolic coil packing density sufficient to either occlude the aneurysm neck or fill the aneurysm sac is difficult and time consuming. Further, aneurysm morphology (e.g. wide neck, bifurcation, etc.) can require ancillary devices such a stents or balloons to support the coil mass and obtain the desired packing density. The coils and accompanying ancillary devices can remain in patients for their entire lives, and can apply damaging stressing forces to the aneurysm. Current embolic coil approaches can also involve the delivery of various coils into a coil mass. With each coil inserted, there is an increased risk for an adverse event. Therefore, there is an advantage to creating a system that does not require multiple products or coils to be inserted during one procedure. Additionally, embolic coils do not always effectively treat aneurysms as re-canalization of the aneurysm and/or coil compaction can occur over time.

One particular type of occlusive approach endeavors to deliver and treat the entrance or "neck" of the aneurysm as opposed to the volume of the aneurysm by implanting a device in the parent vessel of the aneurysm. In such "neck" approaches, by minimizing blood flow across the neck, a cessation of flow into the aneurysm can be achieved. In turn, a thrombotic mass can naturally form without having to deliver embolic materials into the aneurysm sac, as previously described. However, neck-occlusive approaches, such as implanting a flow impeding device in the parent vessel, are not without drawbacks. This type of approach can impede blood flow into peripheral blood vessels while blocking the aneurysm neck in the parent vessel. Impeding flow to the peripheral blood vessel can unintentionally lead to severe damage if the openings of the vessels are blocked.

Another type of occlusive approach is to use glues, adhesives, or other similar products (e.g., NBCA (N-butyl cyanoacrylate)) to obstruct blood flow to areas of the brain. However, these products, when inserted into cranial vessels alone, can move downstream and cause embolization in areas that are not desirable. It is therefore desirable to have a device which easily, accurately, and safely occludes a neck of an aneurysm or other arterio-venous malformation in a parent vessel and can maintain the placement of any glues or adhesives used without requiring the insertion of multiple products or blocking flow into peripheral vessels communicating with the parent vessel while minimizing applied forces to the aneurysm.

It is an aim of this invention to resolve these and other issues of the art.

SUMMARY

Disclosed herein are various exemplary devices for treating an aneurysm with an adhesive cover treatment device. The devices can generally include a net portion for occluding an aneurysm neck and an adhesive to secure the net portion. The devices can further include a channel orifice opening in the net portion, and an agent channel for delivering a rapid-curing agent through the orifice into the aneurysm. Devices can be delivered through a catheter to the aneurysm, the net can expand to occlude the aneurysm neck, the net can be adhered to the aneurysm neck. In devices including a channel orifice and agent channel, the rapid-curing agent can be injected into the aneurysm. During injection of the rapid-curing agent, the net portion can create a barrier to inhibit the rapid-curing agent from exiting the aneurysm. After injection of the coagulation agent, portions of the treatment device, excluding the net portion, can be extracted from the patient.

An example treatment device for occluding an aneurysm can include a net portion that is expandable from a collapsed configuration to an occluding configuration and an adhesive for securing the net portion. The net portion in the occluding configuration can occlude an aneurysm neck to create a barrier between the aneurysm and a blood vessel. The adhesive can secure the net portion in its position in the occluding configuration near the aneurysm neck to prevent the net portion from dislodging and disrupting the barrier between the aneurysm and the blood vessel. When the barrier formed by the net portion is adhered in place, the aneurysm can self-embolize. The example device can be delivered to the aneurysm using a microcatheter.

The adhesive can be activated prior to or subsequent to the net portion reaching the occluding configuration, such as prior to delivery of the net portion to the aneurysm, upon delivery of the net portion to the aneurysm, when the net portion reaches the occluding configuration, or after the net portion reaches the occluding configuration.

An example device for occluding an aneurysm can further include a hypotube spanning at least a portion of the perimeter of the net portion that contains the adhesive in an uncured state. The hypotube can contain at least one hypotube orifice that exposes at least some of the adhesive in the uncured state to an environment outside the net portion. A curing channel can deliver a curing agent to the net portion to activate the adhesive from the uncured state. The adhesive can then adhere the net portion in the occluding configuration in its position occluding the aneurysm neck.

An example device can further include a delivery channel for delivering the adhesive to the net portion. The delivery channel can have a distal end connected to the net portion. The adhesive can be delivered to the net portion prior to or subsequent to the net portion reaching the occluding configuration, such as prior to delivery of the net portion to the aneurysm, upon delivery of the net portion to the aneurysm, when the net portion reaches the occluding configuration, or after the net portion reaches the occluding configuration.

An example device for occluding an aneurysm can further include a channel orifice and an agent channel. The channel orifice can define an opening in the net portion through which the rapid-curing agent can be injected. The channel orifice can open towards the aneurysm when the net portion is in the occluding configuration. The agent channel can be in communication with the channel orifice and can deliver the rapid-curing agent through the channel orifice into the aneurysm sac.

The agent channel can have a proximal end and a distal end. The distal end of the agent channel can communicate with the channel orifice to transfer the rapid-curing agent into the aneurysm sac. The proximal end of the agent channel can receive the rapid-curing agent. The channel orifice can also be an opening in the distal end of the agent channel, whereby a single opening functions as both the channel orifice and the distal end of the agent channel.

The example device can further include a trigger mechanism in communication with the proximal end of the agent channel. The trigger mechanism can communicate with the proximal end of the agent channel to receive the rapid-curing agent or introduce the rapid-curing agent into the agent channel. The trigger mechanism can facilitate delivery of the rapid-curing agent from the proximal end to the distal end of the agent channel, and then through the channel orifice into the aneurysm sac.

An example method for treating an aneurysm can include providing an exemplary treatment device which can include a net portion and an adhesive; delivering the exemplary treatment device to an aneurysm treatment site; expanding the net portion to an occluding configuration at an aneurysm neck to occlude at least a portion of the aneurysm neck to create a barrier between a blood vessel and the aneurysm; and adhering the net portion approximate to the aneurysm neck.

The method can further include inserting the adhesive in an uncured state into a hypotube spanning at least a portion of the perimeter of the net portion, where the hypotube contains at least one hypotube orifice exposing at least some of adhesive the environment outside the net portion; and delivering a curing agent to the net portion via a curing channel to activate the adhesive.

Another example method for treating an aneurysm can include providing an exemplary treatment device which can include a net portion, an adhesive, a channel orifice defining an opening in the net portion, and an agent channel; joining the agent channel to the channel orifice; delivering the exemplary treatment device to an aneurysm treatment site; expanding the net portion to an occluding configuration at an aneurysm neck to occlude at least a portion of the aneurysm neck to create a barrier between a blood vessel and the aneurysm to prevent a rapid-curing agent from entering the blood vessel; adhering the net portion approximate to the aneurysm neck; and delivering the rapid-curing agent through the agent channel, through the channel orifice, and into the aneurysm sac to coagulate the blood present in the aneurysm.

The method can further include providing a trigger mechanism; triggering the delivery of the agent by activating the trigger mechanism at a proximal end of the agent channel; and delivering the agent from the proximal end of the agent channel to a distal end of the agent channel.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIGS. 2a to 2b are illustrations of a treatment sequence of an exemplary treatment device to occlude an aneurysm according to aspects of the present invention;

FIGS. 3a to 3d are illustrations of a treatment sequence of an exemplary treatment device to occlude an aneurysm and deliver a rapid-curing agent to an aneurysm according to aspects of the present invention;

FIG. 8 is a flow diagram outlining example method steps that can be carried out during delivery and use of a treatment device according to aspects of the present invention.

DETAILED DESCRIPTION

The descriptions contained herein are examples of the invention and are not intended in any way to limit the scope of the invention. In general, example devices described herein describe a treatment device that can be placed and adhered over the neck of an aneurysm to create a barrier between the vessel and the aneurysm. At least one rapid-curing agent can then be delivered into the aneurysm sac. The rapid-curing agent can coagulate the blood in the aneurysm instantly.

The example devices can include a net portion that can expand from a collapsed configuration to an occluding configuration in which the net portion in the occluding configuration is shaped to occlude an aneurysm neck. The net portion can be adhered in position to occlude the aneurysm neck. In the occluding configuration, the net portion can generally have a channel orifice working in connection with an agent channel that delivers a rapid-curing agent through the channel orifice and into the aneurysm sac.

It must be noted that, as used in the specification and the appended claims, the singular forms "a," "an" and "the" include plural referents unless the context clearly dictates otherwise. By "comprising" or "containing" or "including" it is meant that at least the named compound, element, particle, or method step is present in the composition or article or method, but does not exclude the presence of other compounds, materials, particles, method steps, even if the other such compounds, material, particles, method steps have the same function as what is named.

In describing examples, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method can be performed in a different order than those described herein without departing from the scope of the disclosed technology. Similarly, it is also to be understood that the mention of one or more components in a device or system does not preclude the presence of additional components or intervening components between those components expressly identified.

Figure 1A:
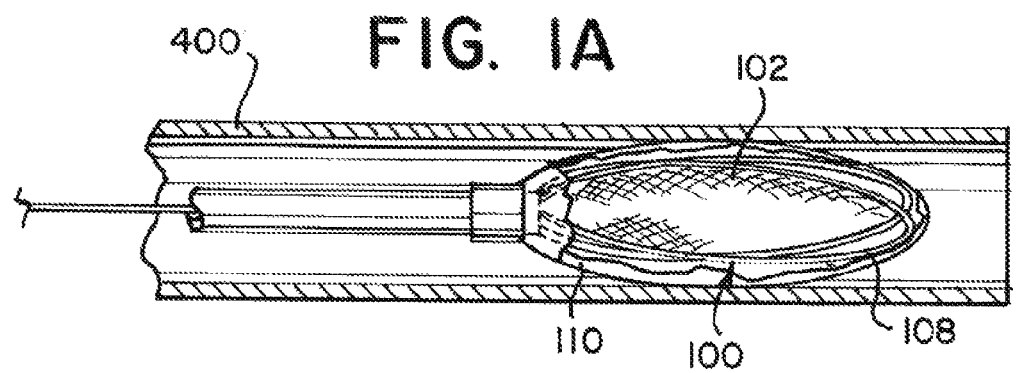
FIGS. 1a to 1c are illustrations of a treatment sequence of an exemplary treatment device to occlude an aneurysm according to aspects of the present invention.
Figure 1B:
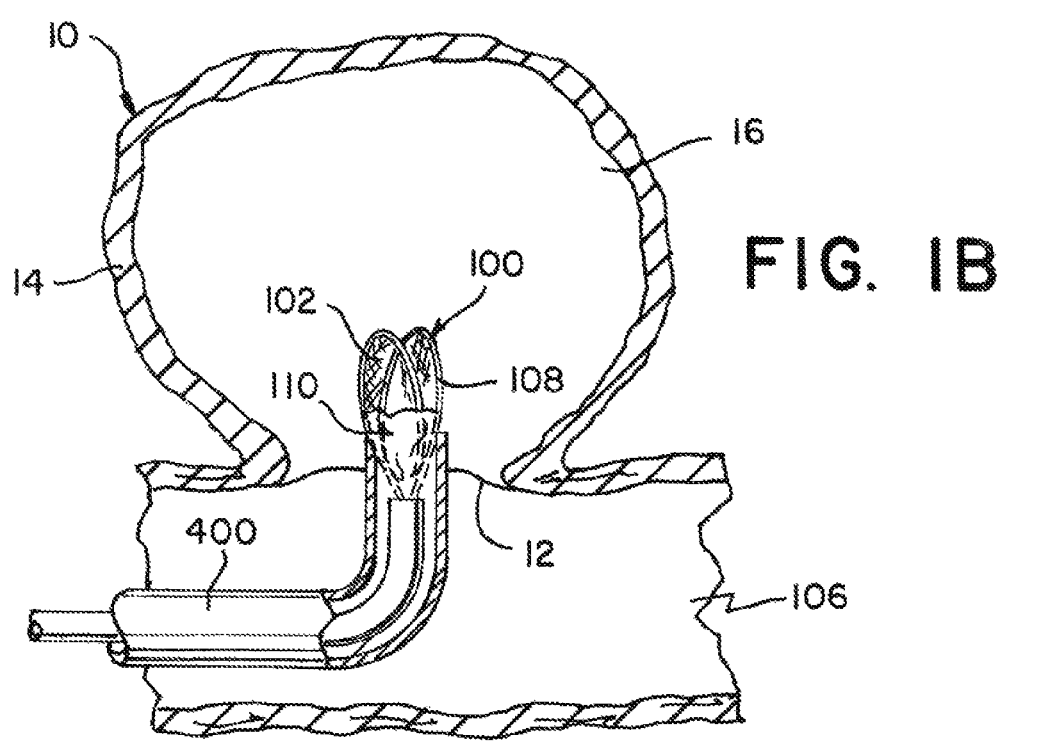
Figure 1C:
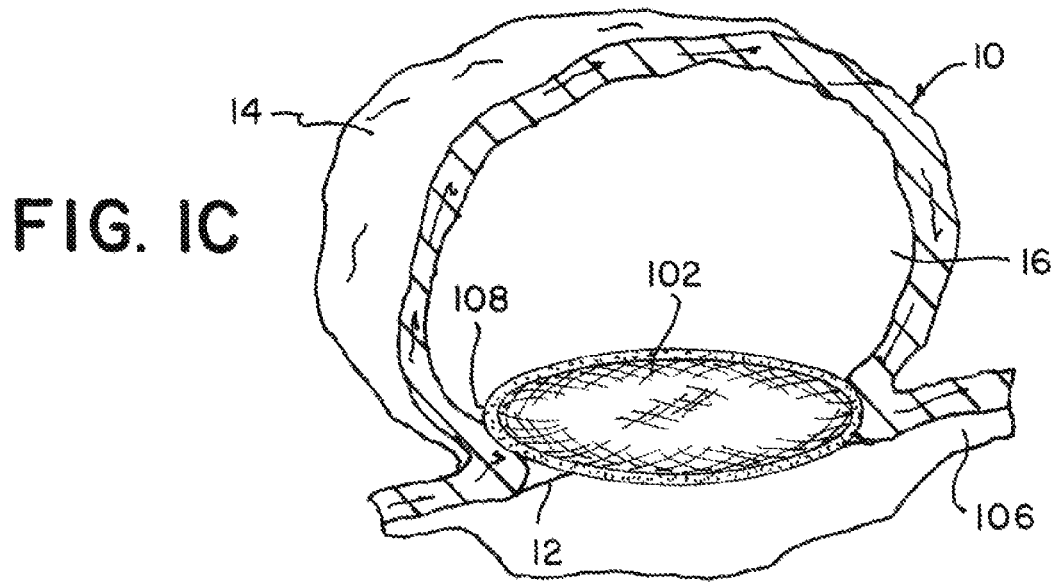

FIGS. 1a through 1c are illustrations of stages or steps that can occur during a treatment sequence of an exemplary treatment device 100 delivered to an aneurysm 10. FIG. 1a is an illustration of an example treatment device 100 wherein a net portion 102 is shown in a collapsed delivery configuration inside a delivery catheter 400. The net portion 102 can have an adhesive agent 108 located on at least a portion of the outer perimeter of the net portion 102, and an adhesive barrier 110 covering the adhesive agent 108. The net portion 102 can be sized to fit within the lumen of a delivery catheter 400 when the net portion 102 is in the collapsed configuration. When the net portion 102 is in the collapsed configuration, the net portion 102 can have sufficient flexibility to be delivered through the delivery catheter 400, navigating torturous anatomical geometries, to be delivered to an aneurysm 10. The net portion 102 in the collapsed configuration can have a substantially tubular shape.

Moving on to FIG. 1b, the treatment device 100 can be delivered to an aneurysm 10 by sliding the device 100 distally when the net portion 102 is in a collapsed configuration through a delivery catheter 400. The treatment device 100 can be delivered to a treatment site through a blood vessel 106. FIG. 1b illustrates the treatment device 100 inside the delivery catheter 400 located near an aneurysm neck 12. FIG. 1b further shows the net portion 102 pushed partially out of the delivery catheter 400 for deployment inside the aneurysm sac 16. The net portion 102 can expand as it exits the delivery catheter 400. The net portion 102 can include a memory shape material such as Nitinol, a Nitinol alloy, a polymer memory shape material, or other memory shape material having properties for reshaping as described herein. The net portion 102 can be in a deformed shape in the collapsed configuration and reshape based on a predetermined shape after exiting the delivery catheter 400. As shown here, upon the net portion 102 exiting the delivery catheter 400, the adhesive barrier 110 can be removed to expose the adhesive agent 108 located on at least a portion of the perimeter of the net portion. Alternatively, the adhesive barrier 110 can be removed at other times prior to or subsequent to the net portion 102 reaching the occluding configuration, such as prior to delivery of the net portion 102 to the aneurysm 10, upon delivery of the net portion 102 to the aneurysm 10, when the net portion 102 reaches the occluding configuration, or after the net portion 102 reaches the occluding configuration. The adhesive agent 108 can include medical grade silicone-based adhesives as well as light-curable adhesives. The adhesive agent 108 can include adhesives such as N-butyl cyanoacrylate (NBCA), Poly (methyl methacrylate) (PMMA996), N-Methyl-2-Pyrrolidone (NMP), Carbonic anhydrase-related protein 10 (CA10), EA/MMA, and DME.

FIG. 1c illustrates the example treatment device 100 wherein the net portion 102 is in an occluding configuration in the aneurysm 10. The net portion 102 in the occluding configuration can be sized to occlude at least a portion of an aneurysm neck 12. The net portion 102 in the occluding configuration can completely occlude the aneurysm neck 12 as depicted in FIG. 1c. The net portion 102 in the occluding configuration can occlude the neck 12 to create a barrier between a blood vessel 106 and the aneurysm 10. The net portion 102 can occlude the aneurysm 10 from inside the aneurysm sac 16. As illustrated in FIG. 1c, the exposed adhesive agent 108 can be in contact with the aneurysm wall 14 when the net portion 102 is in the occluding configuration. In occluding configuration, the net portion 102 can be capable of deflecting a blood flow from the aneurysm 10, diverting a blood flow from the aneurysm 10, slowing a blood flow into the aneurysm 10, or any combination thereof.

In the occluding configuration, the net portion 102 can extend to the aneurysm wall 14, and the adhesive agent 108 can hold the net portion 102 in its position relative to the aneurysm wall 14 and aneurysm neck 12 such that the treatment device 100 doesn't become dislodged and therefore ineffective at inhibiting blood flow into the aneurysm 10. The net portion 102 can also provide a force against the aneurysm wall 14 to help maintain the occluding configuration of the net portion 102 and assist the adhesive agent 108 in adhering to the aneurysm wall 14. For example, the net portion 102 can be made of a memory shape material having a first, predetermined shape and a second, collapsed shape in the collapsed configuration. When the net portion 102 is in an occluding configuration within the aneurysm 10, the net portion 102 can move to a third, deployed shape that is based at least in part on the first, predetermined shape and the anatomical geometry of the aneurysm 10. In the example, the first, predetermined shape can be sized larger than the wall 14 within the aneurysm sac 16; the net portion 102 can move to extend to the wall 14; and the net portion 102 can provide a force against the wall 14 as the properties of the memory shape material cause the net portion 102 to attempt to open to the predetermined shape. This force can help the adhesive agent 108 adhere to the wall to maintain the position of the net portion 102. The net portion 102 in the occluding configuration can take the shape of the aneurysm neck 12 and/or interior walls 14 of the aneurysm near the aneurysm neck 12.

FIG. 2a illustrates the deployment of the net portion 102 in the same manner described in FIG. 1b. FIG. 2a, however, shows the net portion 102 pushed partially out of the delivery catheter 400 for deployment outside the aneurysm sac 16 across the aneurysm neck 12. FIG. 2b illustrates the example treatment device 100 wherein the net portion 102 is in an occluding configuration outside of the aneurysm 10. In this example, the adhesive agent 108 can adhere the net portion 102 to the walls of the blood vessel 106 and over the aneurysm neck 12 to deflect a blood flow from the aneurysm 10, divert a blood flow from the aneurysm 10, slow a blood flow into the aneurysm 10, or any combination thereof. The adhesive agent 108 can hold the net portion 102 in its position over the aneurysm neck 12 such that the treatment device 100 doesn't become dislodged and therefore ineffective at inhibiting blood flow into the aneurysm 10 and becoming a potential blockage elsewhere in the vascular.

Figure 3B:
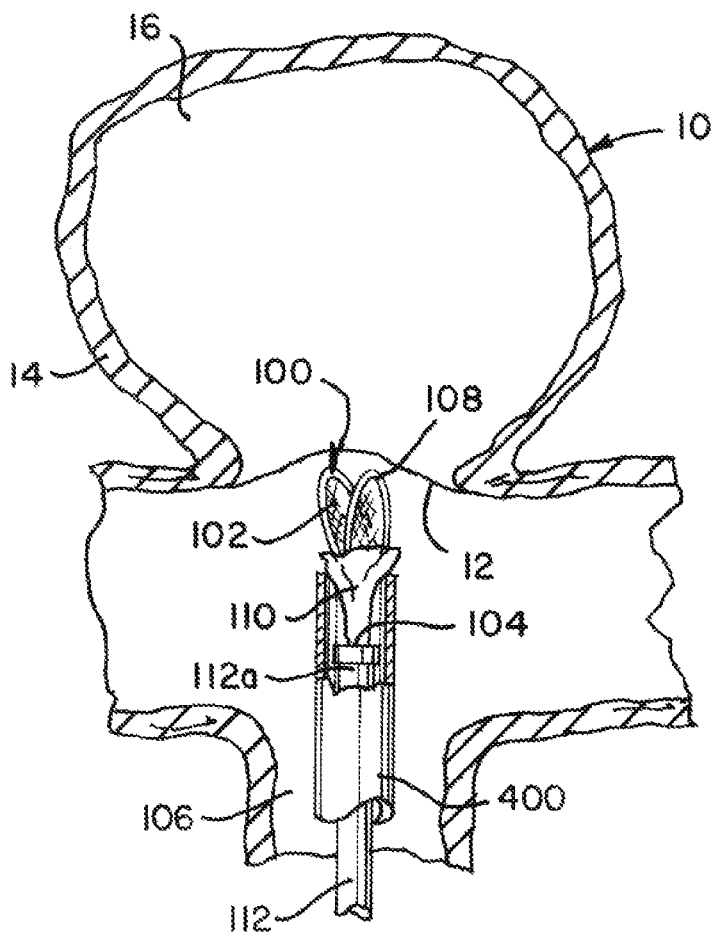
Figure 3C:
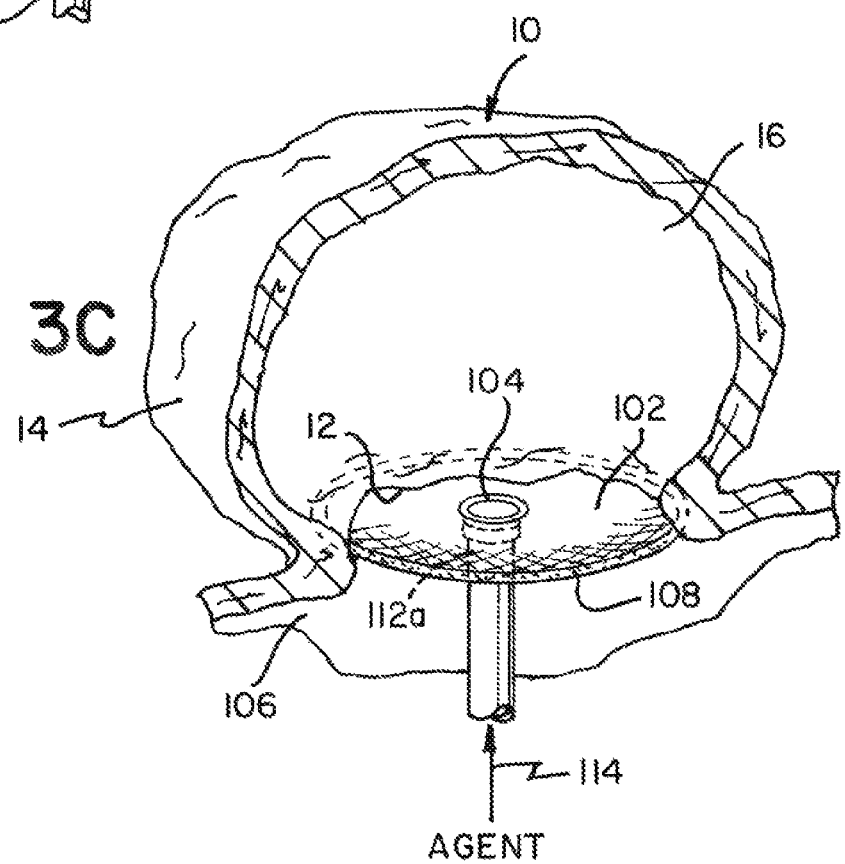

FIGS. 3a through 3c are illustrations of stages or steps that can occur during a treatment sequence of an exemplary treatment device 100 to occlude an aneurysm and deliver a rapid-curing agent 114 to an aneurysm 10. FIG. 3a is an illustration of an example treatment device 100 wherein the net portion 102 with an adhesive agent 108 covered by an adhesive barrier 110 is shown in a collapsed delivery configuration inside a delivery catheter 400, similar to FIG. 1a. The net portion 102 can contain a channel orifice 104 positioned on a proximal end of the collapsed net portion 102. The channel orifice 104 can work in connection with an agent channel 112. The channel orifice 104 can be connected to the distal end 112a of the agent channel 112. The treatment device 100 can be sized to fit within the lumen of a delivery catheter 400 when the net portion 102 is in the collapsed configuration. The agent channel 112 can have sufficient length to be accessible outside of the patient when the net portion 102 reaches a treatment site. The net portion 102 is shown in a collapsed delivery configuration inside a delivery catheter 400.

FIG. 3b illustrates the treatment device 100 inside the delivery catheter 400 with the net portion 102 exiting the delivery catheter 400 for deployment outside a sac 16 of an aneurysm 10, similar to the manner described in FIG. 1b. Alternatively, the net portion 102 can deploy inside the sac 16 of the aneurysm 10. As the device 100 exits the delivery catheter 400, the adhesive agent 108 is exposed in the manner described in FIG. 1b.

FIG. 3c illustrates the treatment device 100 wherein the net portion 102 is in the occluding configuration outside the aneurysm sac 16 similar to FIG. 2b. As illustrated, the channel orifice 104 can be located in the net portion 102 such that the channel orifice 104 opens up to the aneurysm 10. The channel orifice 104 can be centrally located in the net portion 102. The channel orifice 104 in the net portion 102 can work in connection with an agent channel 112. The agent channel 112 can allow for the transfer of one or more rapid-curing agents 114 through the channel 112 to the channel orifice 104. The rapid-curing agent 114 can include agents such as collagen, chitosan, kaolin, zeolite, organic or biocompatible solvents, or other agents having properties for rapid-curing as described herein. The agent channel 112 can have a distal end 112a and a proximal end 112b (see FIG. 6). The distal end 112a of the agent channel 112 can connect to the channel orifice 104. The proximal end 112b can receive the rapid-curing agent 114 into the agent channel 112 and deliver the rapid-curing agent 114 from the proximal end to the distal end 112a connected to the channel orifice 104. The proximal end 112b can be accessible outside of the patient for injection of the rapid-curing agent 114 into the patient. Rapid-curing agent 114 passing through the lumen of the agent channel 112 to the distal end 112a can subsequently pass through the channel orifice 104 and into the aneurysm sac 16 upon reaching the distal end 112a of the agent channel 112. The distal end 112a of the agent channel 112 can also be the channel orifice 104 of the net portion 102. The rapid-curing agent 114 can coagulate the blood inside the aneurysm 10. The rapid-curing agent 114 can coagulate the blood inside the aneurysm 10 virtually instantaneously upon contacting the blood inside the aneurysm 10 according to the coagulation properties of the rapid-curing agent 114.

Figure 3D:
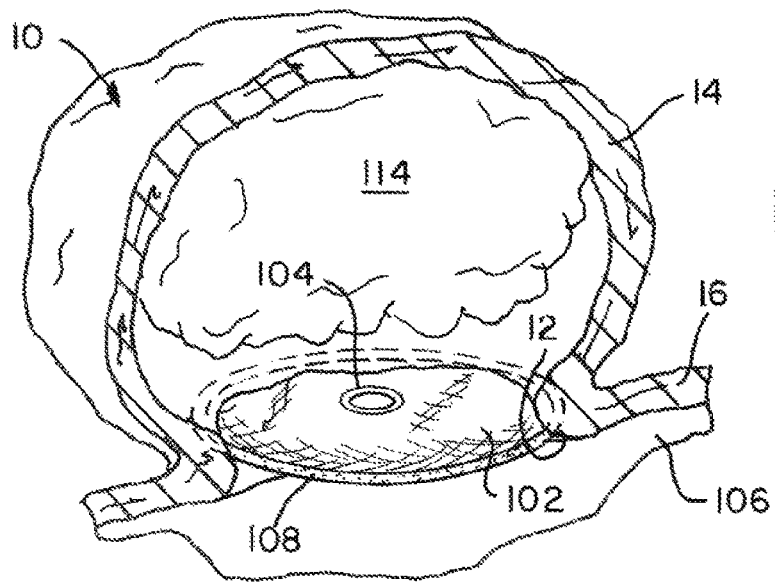

As shown in FIG. 3d, once the rapid-curing agent 114 has been pumped into the aneurysm sac 16, the components of the treatment device 100 (not shown) aside from the net portion 102 can be removed from the aneurysm 10. The components of the treatment device 100 aside from the net portion 102 can be removed once the rapid-curing agent 114 has coagulated the blood in the aneurysm 10. The components of the treatment device 100 aside from the net portion 102 can be sized to traverse through a lumen of a retrieval catheter (not shown).

Figure 4A:
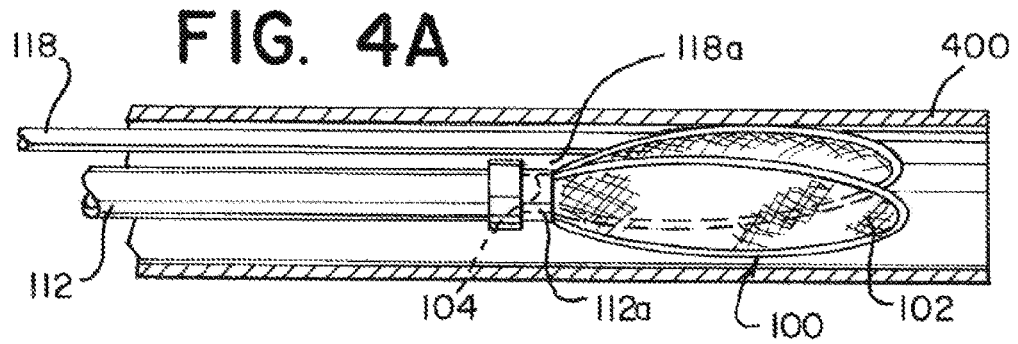
FIGS. 4a to 4d are illustrations of a treatment sequence of an exemplary treatment device to occlude an aneurysm, and deliver an adhesive to a net portion and a rapid-curing agent to an aneurysm according to aspects of the present invention.

FIGS. 4a to 4d are illustrations of stages or steps that can occur during a treatment sequence of an exemplary treatment device 100 to occlude an aneurysm 10, deliver an adhesive 108 to the net portion 102, and deliver a rapid-curing agent 114 to an aneurysm 10. FIG. 4a is an illustration of an example treatment device 100 wherein the net portion 102 is shown in a collapsed delivery configuration inside a delivery catheter 400. The device 100 can have a channel orifice 104 and agent channel 112 as described in FIG. 3a. The device 100 can also have a delivery channel 118 that can work in communication with the net portion 102. The delivery channel 118 can have a distal end 118a in communication with the net portion 102. The delivery channel 108 can deliver adhesive 108 the net portion 102 to adhere the net portion 102 approximate the neck 12. The treatment device 100 can be sized to fit within the lumen of a delivery catheter 400 when the net portion 102 is in the collapsed configuration.

Figure 4B:
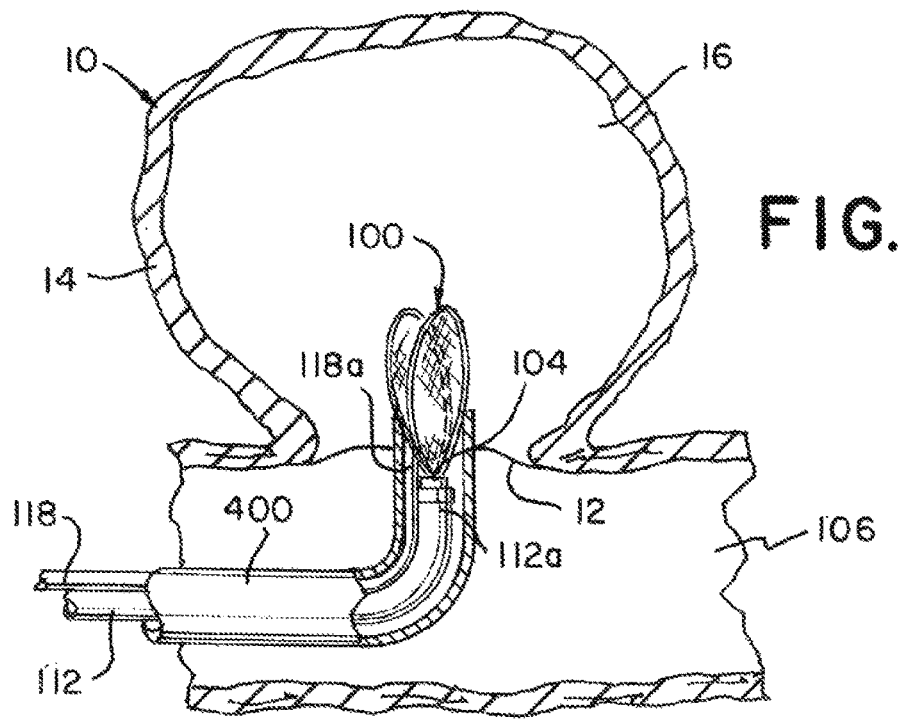

FIG. 4b illustrates the deployment of the net portion 102 inside the sac 16 of an aneurysm 10. As illustrated in FIG. 4b, the treatment device 100 can be delivered to an aneurysm 10 by sliding the device 100 distally when the net portion 102 is in a collapsed configuration through a delivery catheter 400. The treatment device 100 can be delivered to a treatment site through a blood vessel 106. FIG. 4b illustrates the treatment device 100 inside the delivery catheter 400 located near an aneurysm neck 12. FIG. 4b further shows the net portion 102 pushed partially out of the delivery catheter 400 for deployment inside the aneurysm sac 16. The net portion 102 can expand as it exits the delivery catheter 400. Alternatively, the net portion 102 can deploy outside the sac 16 of the aneurysm 10.

Figure 4C:
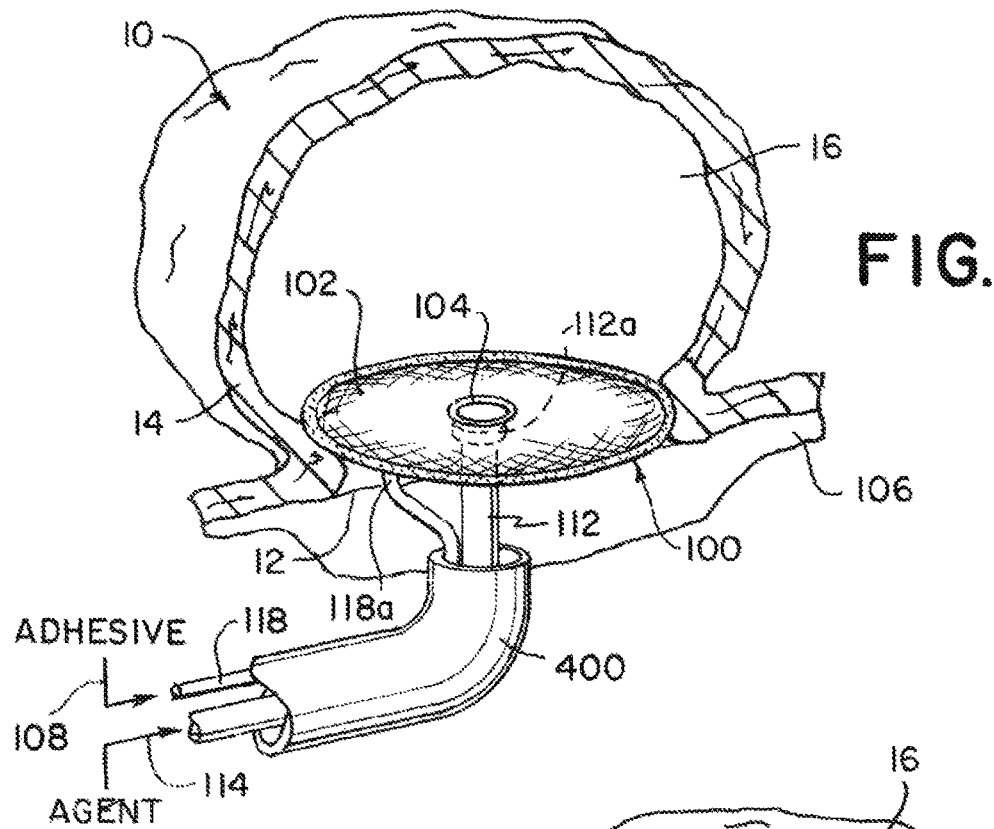

FIG. 4c illustrates the treatment device 100 wherein the net portion 102 is in the occluding configuration inside the aneurysm sac 16. As shown in FIG. 4c, after the net portion 102 reaches the occluding configuration, the adhesive agent 108 can be delivered to the net portion 102 through the delivery channel 118 to adhere the net portion 102 over the aneurysm neck 12 inside the aneurysm sac 16. Alternatively, delivery channel 118 can deliver adhesive 108 to the net portion 102 to adhere the net portion 102 in the occluding configuration over the aneurysm neck 12 outside the aneurysm sac 16. The adhesive 108 can also be delivered prior to or subsequent to the net portion 102 reaching the occluding configuration, such as prior to delivery of the net portion 102 to the aneurysm 10, upon delivery of the net portion 102 to the aneurysm 10, or when the net portion 102 reaches the occluding configuration. After the net portion 102 is adhered over the neck 12, the rapid-curing agent 114 can be delivered to the aneurysm sac 16 in the manner described in FIG. 3c.

Figure 4D:
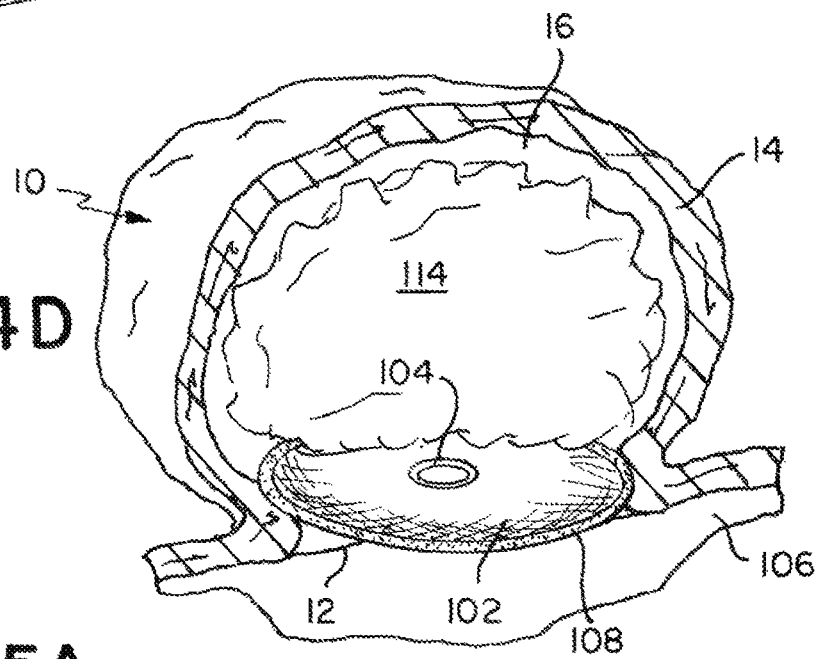

As in FIG. 3d, FIG. 4d illustrates the aneurysm 10 once the rapid-curing agent 114 has been pumped into the aneurysm sac 16, after which the components of the treatment device 100 (not shown) aside from the net portion 102 can be removed from the aneurysm 10.

Figure 5A:
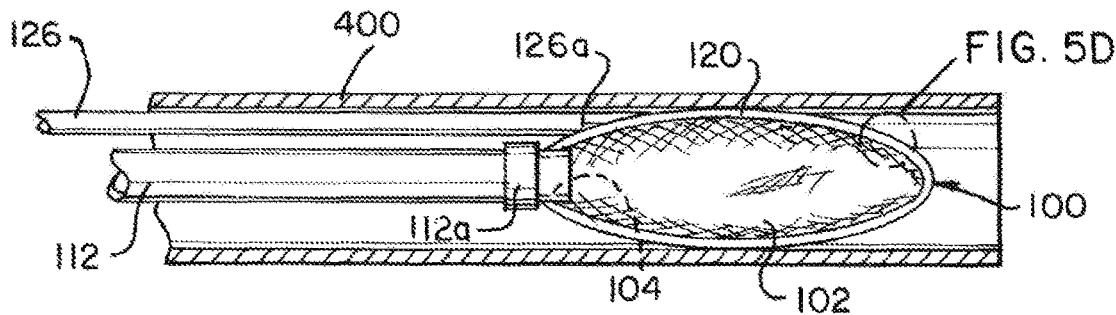
FIGS. 5a to 5g are illustrations of a treatment sequence of an exemplary treatment device to occlude an aneurysm, and deliver a curing agent to a net portion and a rapid-curing agent to an aneurysm according to aspects of the present invention.

FIGS. 5a to 5f are illustrations of stages or steps that can occur during a treatment sequence of an exemplary treatment device 100 to occlude an aneurysm 10, deliver a curing agent 124 to the net portion 102, and deliver a rapid-curing agent 114 to an aneurysm 10. FIG. 5a is an illustration of an example treatment device 100 wherein the net portion 102 is shown in a collapsed delivery configuration inside a delivery catheter 400. The device 100 can have a channel orifice 104 and agent channel 112 as described in FIG. 3a. The device 100 can also have a hypotube 120 spanning at least a portion of the perimeter of the net portion 102. The hypotube 120 can span the entire perimeter of the net portion 102. The hypotube 120 can contain an adhesive 108 in an uncured state. The hypotube 120 can contain one or more hypotube orifices 122 (see FIG. 5d) that expose the uncured adhesive 108 to the environment outside the hypotube 120.

The device 100 can further have a curing channel 126 that can work in communication with the net portion 102. The curing channel 126 can have a distal end 126a in connection with net portion 102. The curing channel 126 can deliver a curing agent (as discussed above) to the net portion 102 of the device 100. The curing agent 126 can activate the uncured adhesive 108 in the net portion 102. The treatment device 100 in its entirety can be sized to fit within the lumen of a delivery catheter 400 when the net portion 102 is in the collapsed configuration.

Figure 5B:
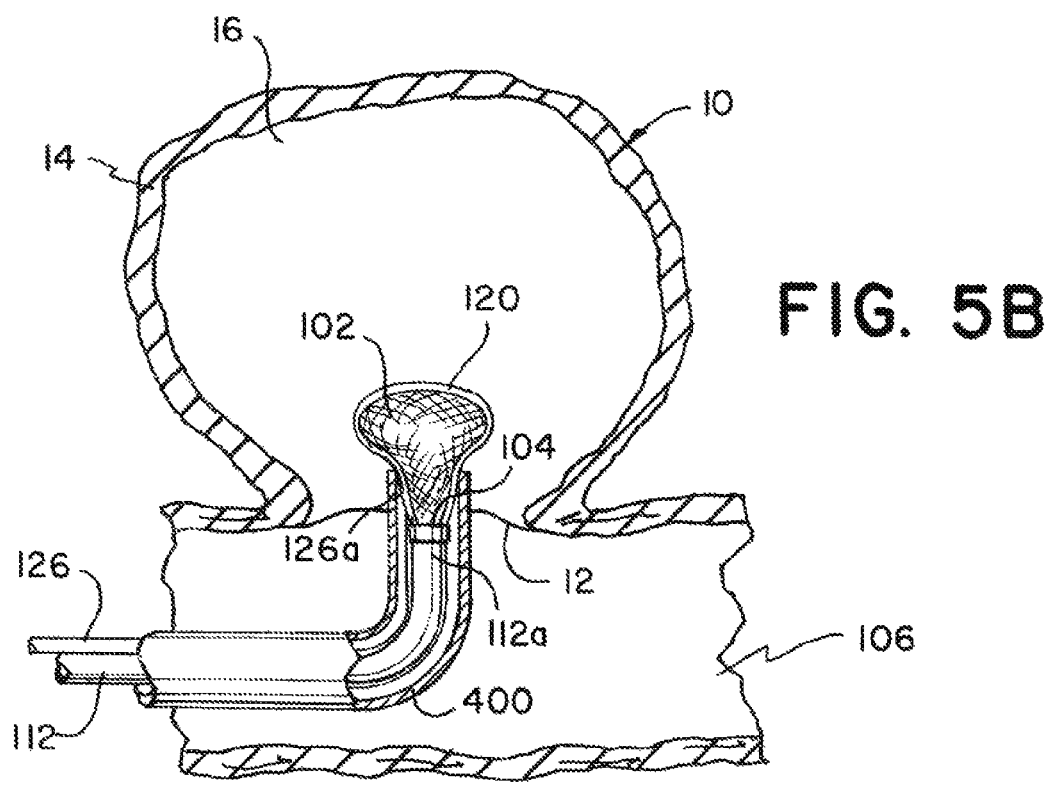
Figure 5C:
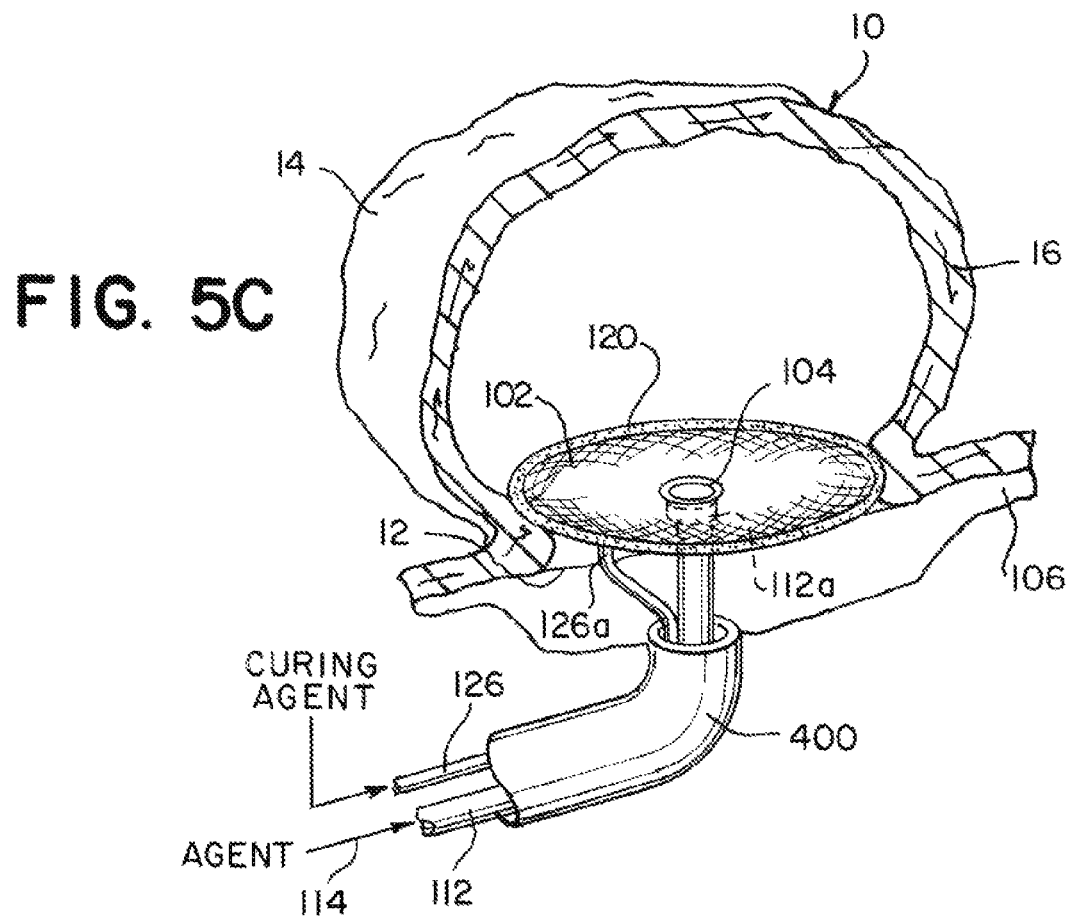

FIG. 5b illustrates the deployment of the net portion 102 inside the sac 16 of an aneurysm 10 similar to FIG. 4b. FIG. 5c illustrates the treatment device 100 wherein the net portion 102 is in the occluding configuration inside the aneurysm sac 16 in the manner shown in FIG. 4c. As shown here, after the net portion 102 reaches the occluding configuration, the curing agent 124 can be delivered to the net portion 102 through the curing channel 126 to activate the adhesive agent 108 and adhere the net portion 102 over the aneurysm neck 12 inside the aneurysm sac 16. Alternatively, the curing agent 124 can be delivered to the net portion 102 through the curing channel 126 to activate the adhesive agent 108 and adhere the net portion 102 over the aneurysm neck 12 outside the aneurysm sac 16. The curing agent 124 can be delivered prior to or subsequent to the net portion 102 reaching the occluding configuration, such as prior to delivery of the net portion 102 to the aneurysm 10, upon delivery of the net portion 102 to the aneurysm 10, or when the net portion 102 reaches the occluding configuration.

Figure 5D:
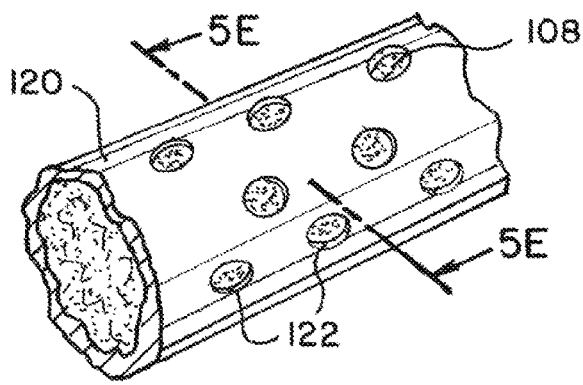
Figure 5E:
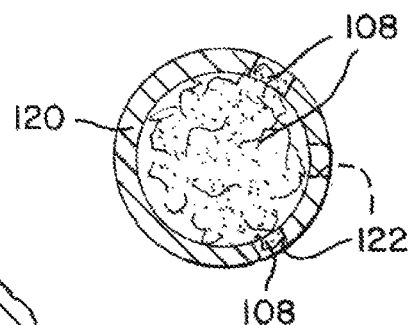
Figure 5F:
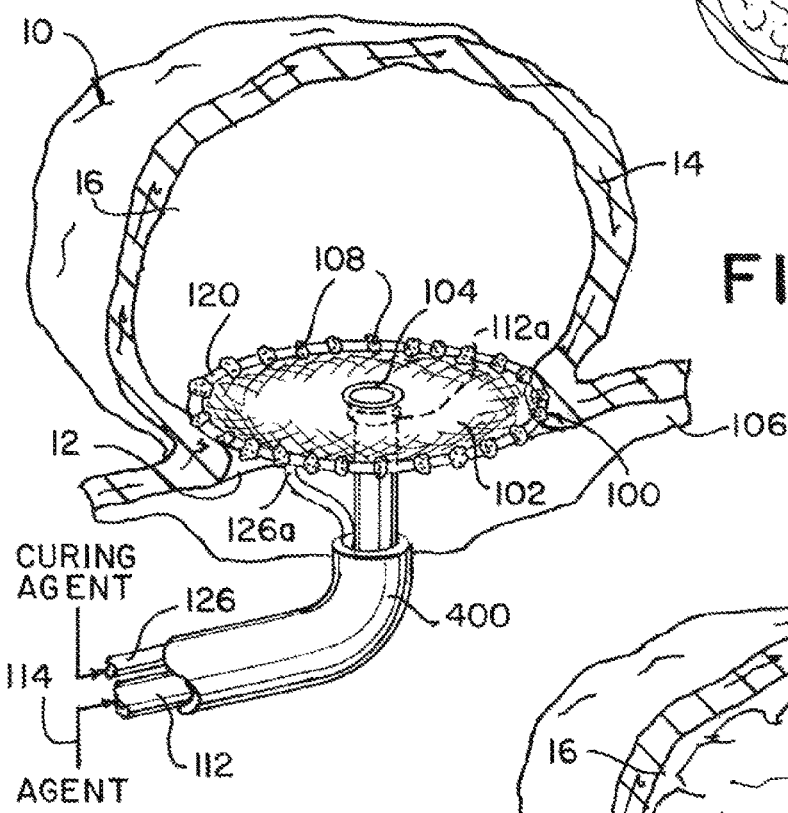
Figure 5G:
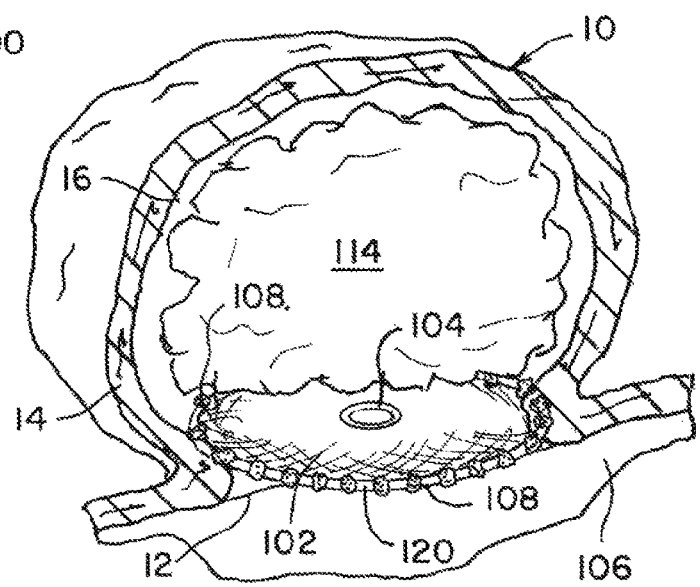

FIG. 5d shows a blown-up and cross-sectional view of the hypotube 120. The hypotube 120 can contain at least one hypotube orifice 122 as well as the adhesive 108 in an uncured state. The hypotube orifices 122 can expose the uncured adhesive 108 to the environment outside the hypotube 120. FIG. 5e is a cross section of net portion 102 loaded with adhesive 108. For example, in FIGS. 5d and 5e, the uncured adhesive 108 can be delivered by first being mechanically held within the net portion 102. The net portion 102 can contain a lumen along the circumference (a hypotube 122) with orifices that allow the uncured adhesive to be exposed. The viscosity of the adhesive 108 can be characterized such that it could be injected into a lumen of the net portion 102 but viscous enough that it will not relocate or disperse during delivery. Upon placing the net portion 102 and later delivering a curing agent, the adhesive within the net will be activated. The net would have orifices that expose some of the adhesive to the aneurysm, allowing it to adhere the edges of the net to the aneurysm wall. In this case, the net would act as the device blocking flow into the aneurysm FIG. 5f illustrates the treatment device 100 wherein the net portion 102 is in the occluding configuration inside the aneurysm sac 16 in the manner shown in FIG. 4c. When the curing agent 124 is delivered to the net portion 102, the adhesive 108 can cure and adhere the net portion 102 in the occluding configuration over the aneurysm neck 12 to occlude the aneurysm 10. Once the net portion 102 has been adhered in position, the rapid curing agent 114 can be delivered to the aneurysm 10 as illustrated in FIG. 3c Similar to FIG. 3d, FIG. 5g illustrates the aneurysm 10 once the rapid-curing agent 114 has been pumped into the aneurysm sac 16, after which the components of the treatment device 100 aside from the net portion 102 are removed from the aneurysm 10.

FIGS. 6a to 6e are illustrations of stages or steps that can occur during another example implementation sequence of an exemplary treatment device 100 to occlude an aneurysm 10 and deliver a rapid-curing agent 114 to an aneurysm 10.

Figure 6A:
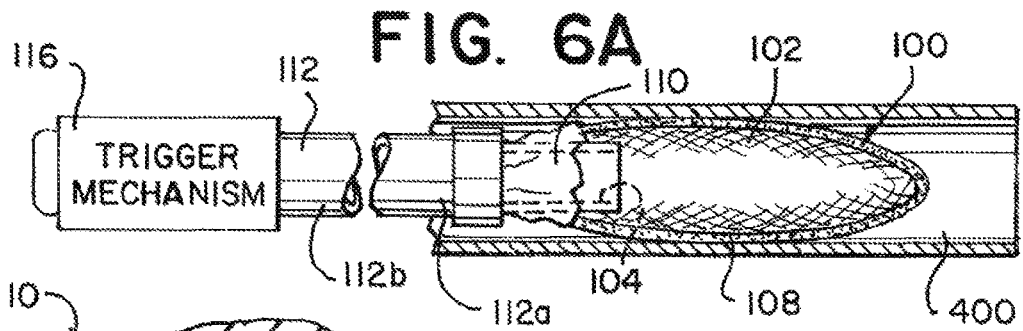
FIGS. 6a to 6d are illustrations of a treatment sequence of an exemplary treatment device in connection with a trigger mechanism to occlude an aneurysm and deliver a rapid-curing agent to an aneurysm according to aspects of the present invention.

FIG. 6a is an illustration of an example treatment device 100 including a net portion 102, a channel orifice 104, an agent channel 112, and a trigger mechanism 116. The net portion 102 is shown in a collapsed delivery configuration inside a delivery catheter 400. The net portion 102 can contain the channel orifice 104 that can be in communication with an agent channel 112. The agent channel 112 can have a proximal end 112b in communication with the trigger mechanism 116. The proximal end 112b of the agent channel 112 can receive the rapid-curing agent 114 into the agent channel 112 for delivery. The trigger mechanism 116 can facilitate the delivery of the rapid-curing agent 114 to an aneurysm sac 16. The components of the treatment device 100 excluding the trigger mechanism 116 can be sized to fit within the lumen of a delivery catheter 400 when the net portion 102 is in the collapsed configuration.

Figure 6B:
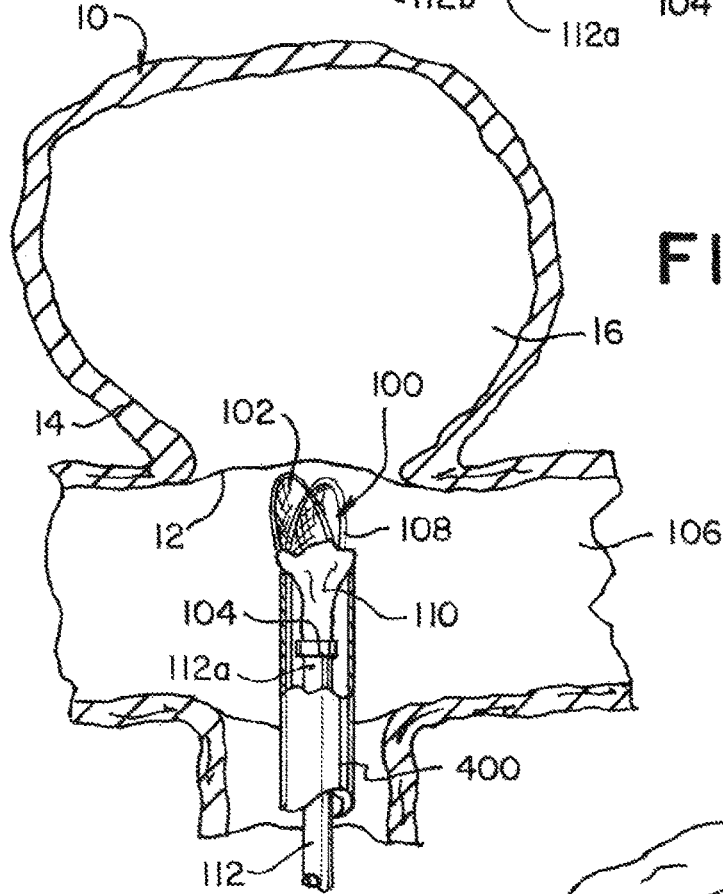
Figure 6C:
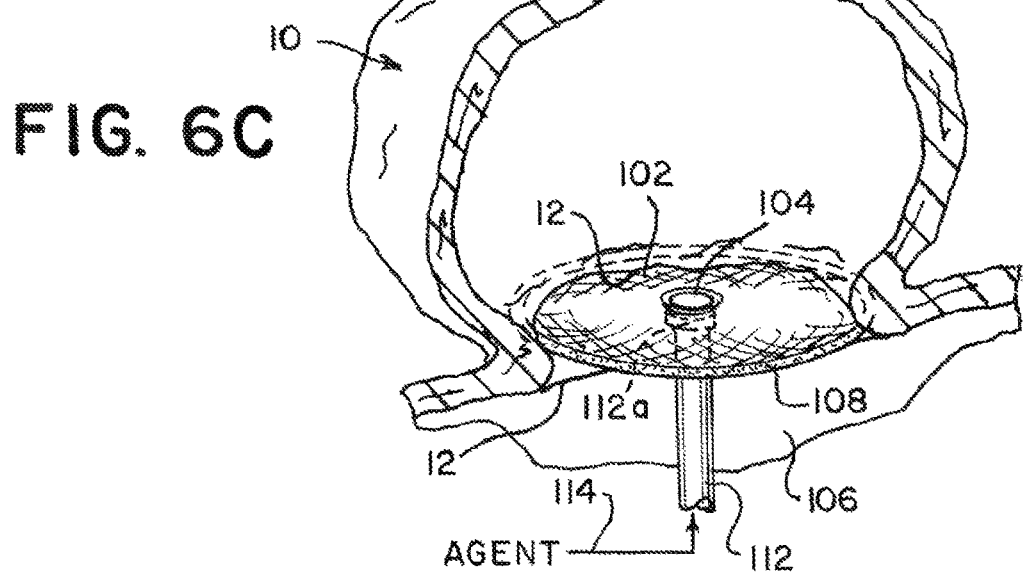
Figure 6D:
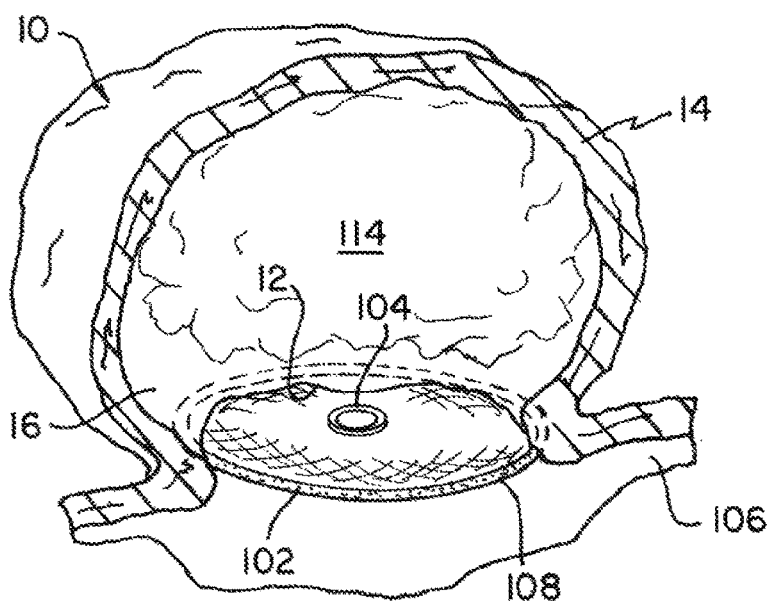

FIG. 6b illustrates the treatment device 100 inside the delivery catheter 400 with the net portion 102 exiting the delivery catheter 400 for deployment outside the aneurysm sac 16 in a manner similar to FIG. 4b. As illustrated in FIGS. 6b to 6d, the treatment site can include an aneurysm 10 positioned adjacent bifurcated blood vessel branches and the treatment device 100 can be delivered to the aneurysm 10 through a stem branch 106 feeding the bifurcated blood vessel branches.

FIG. 6c illustrates the treatment device 100 wherein the net portion 102 is in an occluding configuration in the aneurysm 10. Upon the net portion 102 reaching the occluding configuration, the trigger mechanism 116 can facilitate the delivery of the rapid-curing agent 114 through the agent channel 112 to the aneurysm sac 16.

As in FIG. 3d, FIG. 6d illustrates the aneurysm 10 once the rapid-curing agent 114 has been pumped into the aneurysm sac 16, after which the components of the treatment device 100 aside from the net portion 102 can be removed from the aneurysm 10.

Figure 7:
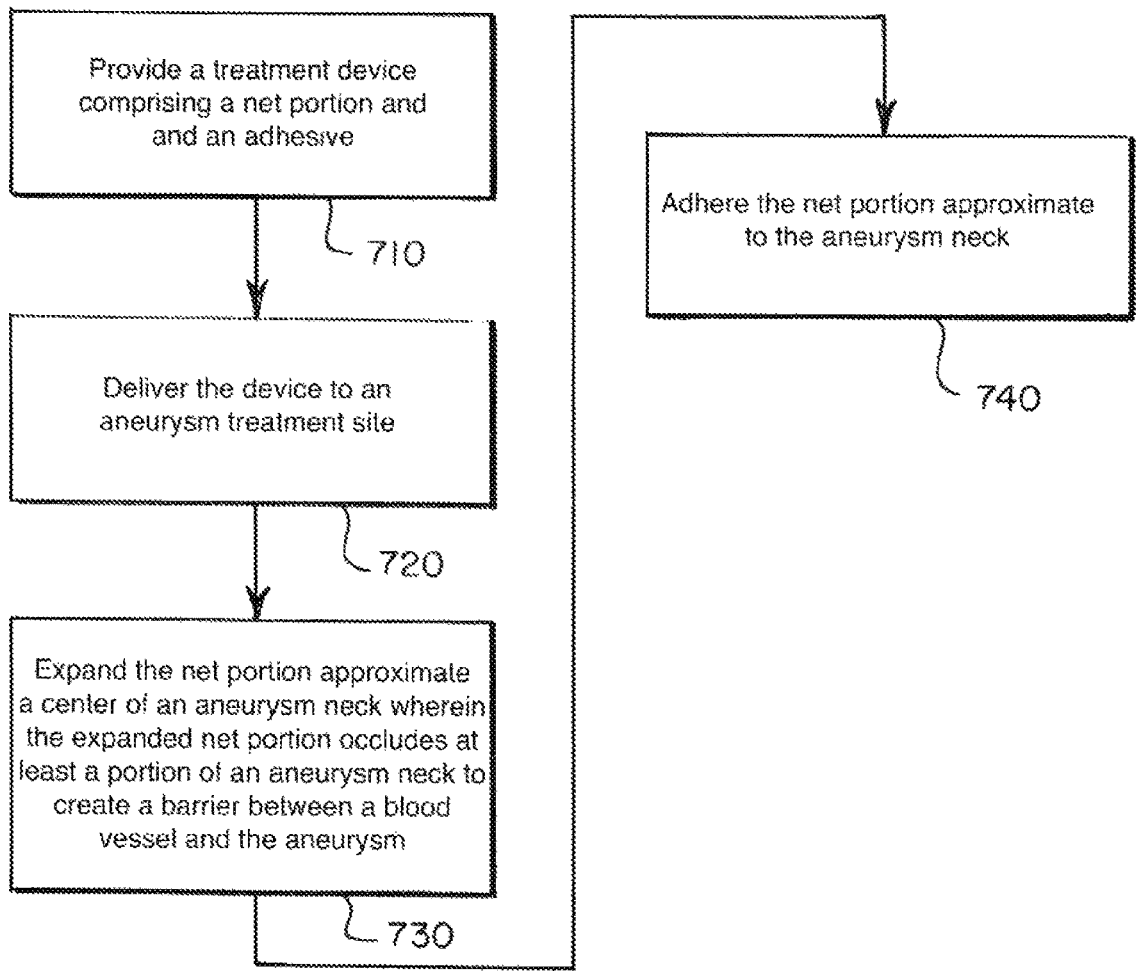
FIG. 7 is a flow diagram outlining example method steps that can be carried out during delivery and use of a treatment device according to aspects of the present invention.

FIG. 7 is a flow diagram outlining example method steps that can be carried out during the administration of a treatment device 100. The method steps can be implemented by any of the example means described herein or by any means that would be known to one of ordinary skill in the art.

Referring to a method 700 outlined in FIG. 7, in step 710 a treatment device comprising a net portion and an adhesive can be provided for administration to a patient. In step 720, the treatment device can be delivered to the aneurysm treatment site. In step 730, the net portion can be expanded to an occluding configuration approximate a center of an aneurysm neck, wherein the expanded net portion occludes at least a portion of the aneurysm neck to create a barrier between a blood vessel and the aneurysm. In step 740, the net portion can be adhered approximate to the aneurysm neck.

Method 700 can further comprise the steps of inserting the adhesive in an uncured state into a hypotube spanning at least a portion of the perimeter of the net portion, wherein the hypotube comprises at least one hypotube orifice exposing a portion of the adhesive in the uncured state to the environment outside the net portion, and delivering a curing agent to the net portion via a curing channel to activate the adhesive.

FIG. 8 is a flow diagram outlining example method steps that can be carried out during the administration of a treatment device 100. The method steps can be implemented by any of the example means described herein or by any means that would be known to one of ordinary skill in the art.

Referring to a method 800 outlined in FIG. 8, in step 810 the treatment device comprising a net portion, an adhesive, a channel orifice defining an opening in the net portion, and an agent channel can be provided for administration to a patient. In step 820, the agent channel can be joined to communicate with the channel orifice. In step 830, the treatment device can be delivered to an aneurysm treatment site. In step 840, the net portion can be expanded to the occluding configuration approximate a center of an aneurysm neck. When the net portion is expanded to the occluding configuration in step 840, the net portion can occlude at least a portion of an aneurysm neck. Step 840 can also create a barrier between a blood vessel 106 and the aneurysm to prevent the rapid-curing agent from entering the blood vessel. In step 850, net portion can be adhered approximate to the aneurysm neck. In step 860, the rapid-curing agent can be delivered through the agent channel and the channel orifice into the aneurysm sac to coagulate the blood present in the aneurysm.

Method 800 can further comprise the steps of providing a trigger mechanism and triggering the delivery of the agent by activating the trigger mechanism at a proximal end of the agent channel to deliver the agent from the proximal end of the agent channel to a distal end of the agent channel.

It should be apparent to those skilled in the art that the present teachings cover devices with any possible combination of a net portion, adhesive, channel orifice, agent channel, hypotube, delivery channel, curing channel, and/or trigger mechanism. The descriptions contained herein are examples of the invention and are not intended in any way to limit the scope of the invention. As described herein, the invention contemplates many variations and modifications of the device for occluding an aneurysm, including alternative geometries of elements and components described herein, utilizing any number of known means for braiding, knitting, weaving, or otherwise forming the net portion as is known in the art, utilizing any of numerous materials for each component or element (e.g. radiopaque materials, memory shape materials, etc.), utilizing additional components including components to deliver a treatment device to an aneurysm or eject an treatment device from a delivery catheter, or utilizing additional components to perform functions not described herein, for example. These modifications would be apparent to those having ordinary skill in the art to which this invention relates and are intended to be within the scope of the claims which follow.

The invention claimed is:

1. A treatment device for treating an aneurysm comprising:
    a net portion expandable from a collapsed configuration to an occluding configuration, the occluding configuration sized to extend across and occlude at least a portion of a neck of the aneurysm to create a barrier between a blood vessel and the aneurysm;
    an adhesive circumscribing at least a portion of a perimeter of the net portion when the net portion is in the occluding configuration, the adhesive being positioned to contact with tissue approximate the aneurysm neck thereby securing the net portion in a position approximate the aneurysm neck; and
    a hypotube containing the adhesive in an uncured state and circumscribing at least a portion of the perimeter of the net portion when the net portion is in the occluding configuration, the hypotube comprising at least one orifice configured to expose a portion of the adhesive in the uncured state to the tissue approximate the aneurysm neck.

2. The treatment device of claim 1 wherein the net portion in the collapsed configuration is sized to traverse through a lumen of a delivery catheter.

3. The treatment device of claim 1 wherein the adhesive is activated subsequent to the net portion reaching the occluding configuration.

4. The treatment device of claim 1 wherein the adhesive is activated prior to the net portion reaching the occluding configuration.

5. The treatment device of claim 4 further comprising a delivery channel delivering the adhesive to the net portion, the delivery channel comprising a distal end connected to the net portion.

6. The treatment device of claim 5 wherein the adhesive is delivered to the net portion through the delivery channel prior to the net portion reaching the occluding configuration.

7. The treatment device of claim 5 wherein the adhesive is delivered to the net portion through the delivery channel subsequent to the net portion reaching the occluding configuration.

8. The treatment device of claim 4 further comprising:
    a channel orifice defining an opening in the net portion, wherein in the occluding configuration the channel orifice is open to the aneurysm; and
    an agent channel in communication with the channel orifice delivering a rapid-curing agent to an aneurysm sac through the channel orifice.

9. The treatment device of claim 8 further comprising:
    a trigger mechanism for introducing the rapid-curing agent into the agent channel;
    wherein the agent channel comprises a proximal end in communication with the trigger mechanism to receive the rapid-curing agent into the agent channel and a distal end in communication with the channel orifice; and
    wherein the agent channel delivers the rapid-curing agent from the proximal end to the distal end and through the channel orifice into the sac of the aneurysm.

10. The treatment device of claim 8 wherein the adhesive is activated prior to the net portion reaching the occluding configuration.

11. The treatment device of claim 8 wherein the adhesive is activated subsequent to the net portion reaching the occluding configuration.

12. The treatment device of claim 8 further comprising a delivery channel delivering the adhesive to the net portion, the delivery channel comprising a distal end connected to the net portion.

13. The treatment device of claim 12 wherein the adhesive is delivered to the net portion through the delivery channel prior to the net portion reaching the occluding configuration.

14. The treatment device of claim 12 wherein the adhesive is delivered to the net portion through the delivery channel subsequent to the net portion reaching the occluding configuration.

15. The treatment device of claim 12 further comprising:
a trigger mechanism for introducing the rapid-curing agent into the agent channel;
   wherein the agent channel comprises a proximal end in communication with the trigger mechanism to receive the rapid-curing agent into the agent channel and a distal end in communication with the channel orifice; and
   wherein the agent channel delivers the rapid-curing agent from the proximal end to the distal end and through the channel orifice into the sac of the aneurysm.

16. A method for treating an aneurysm comprising
providing a treatment device comprising a net portion and an adhesive;
delivering the treatment device to an aneurysm treatment site;
expanding the net portion to an occluding configuration approximate a center of an aneurysm neck, wherein the expanded net portion occludes at least a portion of the aneurysm neck to create a barrier between a blood vessel and the aneurysm;
inserting the adhesive in an uncured state into a hypotube circumscribing at least the portion of a perimeter of the net portion, wherein the hypotube comprises at least one hypotube orifice configured to expose a portion of the adhesive in the uncured state to tissue approximate the aneurysm neck;
delivering a curing agent to the net portion via a curing channel to activate the adhesive; and
adhering the net portion approximate to the aneurysm neck by the adhesive.

17. A method for treating an aneurysm comprising:
providing a treatment device comprising a net portion, a hypotube circumscribing at least a portion of a perimeter of the net portion when the net portion is in an occluding configuration, a channel orifice defining an opening in the net portion, and an agent channel;
joining the agent channel with the channel orifice;
delivering the treatment device to an aneurysm treatment site;
expanding the net portion to the occluding configuration approximate a center of an aneurysm neck, wherein the expanded net portion occludes at least a portion of the aneurysm neck to create a barrier between a blood vessel and the aneurysm to prevent a rapid-curing agent from entering the blood vessel;
adhering the net portion approximate to the aneurysm neck by an adhesive delivered, in an uncured state, through the hypotube such that the adhesive exits the hypotube through at least one orifice of the hypotube and, upon exiting the hypotube, the adhesive contacts tissue approximate the aneurysm neck; and
delivering the rapid-curing agent through the agent channel and the channel orifice into the aneurysm sac to coagulate the blood present in the aneurysm.

18. The method of claim 17 further comprising the steps of:
providing a trigger mechanism;
triggering the delivery of the rapid-curing agent by activating the trigger mechanism at a proximal end of the agent channel; and
delivering the agent from the proximal end of the agent channel to a distal end of the agent channel.

\* \* \* \* \*